United States Patent
Shi

(10) Patent No.: US 12,239,853 B2
(45) Date of Patent: Mar. 4, 2025

(54) SYSTEMS AND METHODS FOR MODELING RADIATION SOURCE

(71) Applicant: SHANGHAI UNITED IMAGING HEALTHCARE CO., LTD., Shanghai (CN)

(72) Inventor: Zhi Shi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 232 days.

(21) Appl. No.: 18/157,792

(22) Filed: Jan. 20, 2023

(65) Prior Publication Data

US 2023/0149742 A1  May 18, 2023

Related U.S. Application Data

(63) Continuation of application No. PCT/CN2020/109005, filed on Aug. 13, 2020.

(51) Int. Cl.
*A61N 5/10* (2006.01)

(52) U.S. Cl.
CPC ......... *A61N 5/1075* (2013.01); *A61N 5/1031* (2013.01); *A61N 5/1071* (2013.01);
(Continued)

(58) Field of Classification Search
CPC .. A61N 5/1075; A61N 5/1031; A61N 5/1071; A61N 2005/1034;
(Continued)

(56) References Cited

U.S. PATENT DOCUMENTS

| | | | |
|---|---|---|---|
| 2010/0082294 A1 | 4/2010 | Adnani | |
| 2020/0066409 A1 | 2/2020 | Gasser et al. | |

FOREIGN PATENT DOCUMENTS

| | | | |
|---|---|---|---|
| CN | 1438602 A | 8/2003 | |
| CN | 1927123 A | 3/2007 | |

(Continued)

OTHER PUBLICATIONS

Townson et al. "GPU-based Monte Carlo radiotherapy dose calculation using phase-space sources", IOP Publishing, Phys. Med. Biol. 58, 2013, p. 4341-4356. (Year: 2013).*

(Continued)

*Primary Examiner* — Dani Fox
*Assistant Examiner* — Mamadou Faye
(74) *Attorney, Agent, or Firm* — METIS IP LLC

(57) ABSTRACT

Systems and methods for determining a target multi-source model of a radiation source corresponding to an energy spectrum is provided. The systems may obtain an initial multi-source model of the radiation source, which includes an initial phase space file that includes information of a plurality of simulated particles of a plurality of energy levels. The systems may estimate, based on the initial phase space file, a plurality of component PDD curves corresponding to the plurality of energy levels. The systems may obtain a measured PDD curve corresponding to radiation of the energy spectrum. For each energy level, the systems may determine, based on the plurality of component PDD curves and the measured PDD curve, a weight for the each energy level. The systems may further determine the target multi-source model of the radiation source based at least in part on the initial multi-source model and the weights.

20 Claims, 14 Drawing Sheets

(52) U.S. Cl.
CPC .............. *A61N 2005/1034* (2013.01); *A61N 2005/1035* (2013.01); *A61N 2005/1076* (2013.01); *A61N 2005/1089* (2013.01)

(58) Field of Classification Search
CPC .... A61N 2005/1035; A61N 2005/1076; A61N 2005/1089; A61N 5/103; G06F 30/20; G06F 2111/08; G06F 2111/10
See application file for complete search history.

(56) References Cited

FOREIGN PATENT DOCUMENTS

| | | |
|---|---|---|
| CN | 101477202 A | 7/2009 |
| CN | 101477205 A | 7/2009 |
| CN | 102921115 A | 2/2013 |
| CN | 104043203 A | 9/2014 |
| CN | 105457170 A * | 4/2016 |
| CN | 105468883 A | 4/2016 |
| CN | 105825067 A | 8/2016 |
| CN | 105866821 A | 8/2016 |
| CN | 106291650 A | 1/2017 |
| CN | 107072624 A | 8/2017 |
| JP | 2016223876 A | 12/2016 |

OTHER PUBLICATIONS

Translation of CN105457170A (Year: 2016).*
The First Office Action in Chinese Application No. 202080104244.8 mailed on Apr. 29, 2024, 41 pages.
International Search Report in PCT/CN2020/109005 mailed on May 17, 2021, 7 pages.
Written Opinion in PCT/CN2020/109005 mailed on May 17, 2021, 6 pages.

* cited by examiner

600

| 610 | Obtaining an initial multi-source model of a radiation source corresponding to an energy spectrum including a plurality of energy levels, the radiation source including at least a primary source and an electron applicator |

↓

| 620 | Determining a weight for each of the plurality of energy levels based on a plurality of estimated component PDD curves in a phantom corresponding to the plurality of energy levels and a measured PDD curve in the phantom corresponding to a radiation of the energy spectrum traversing the phantom |

↓

| 630 | Determining parameters of a primary virtual source of the initial multi-source model based on a simulated OAR curve and a measured OAR curve corresponding to the radiation of the energy spectrum traversing the phantom |

↓

| 640 | Determining a correction coefficient for an electron applicator operably coupled to the primary source |

↓

| 650 | Determining a target multi-source model of the radiation source corresponding to the energy spectrum based at least on the initial multi-source model, the weights, the parameters of the primary virtual source, and the correction coefficient |

Estimating, based on an initial phase space file of an initial multi-source model, a plurality of component PDD curves in a phantom corresponding to a plurality of energy levels of an energy spectrum ~810

Obtaining a measured PDD curve in the phantom corresponding to radiation of the energy spectrum traversing the phantom ~820

Determining, based on the plurality of component PDD curves, a combined PDD curve by adjusting at least one of a group of initial weights until a first difference between the combined PDD curve and the measured PDD curve is below a first threshold ~830

Determining, based on the adjusted group of weights, the weight for each of the plurality of energy levels ~840

Obtaining an output coefficient corresponding to each of a plurality of electron applicators ~1110

Determining a simulated output coefficient corresponding to each of the plurality of electron applicators based on structural parameters of the electron applicator ~1120

Determining a correction coefficient for each of the plurality of electron applicator based on the output coefficient and the simulated output coefficient ~1130

Obtaining structural parameters of an electron applicator of a radiation source — 1210

↓

Obtaining a target multi-source model of the radiation source corresponding to an energy spectrum — 1220

↓

Determining, based on the target multi-source model and the structural parameters of the electron applicator, a phase space file including information of a plurality of simulated particles corresponding to radiation of the radiation source — 1230

↓

Obtaining a transmission model of the radiation of the energy spectrum traversing an object — 1240

↓

Determining a dose distribution in the object based on the phase space file and the transmission model — 1250

Determining positions and directions of a plurality of simulated particles and directions of the plurality of simulated particles based on structural parameters of an electron applicator ~1310

Determining energies of the plurality of simulated particles based on a target multi-source model ~1320

Determining a phase space file based on the positions, the directions, and the energies ~1330

FIG. 13

SYSTEMS AND METHODS FOR MODELING RADIATION SOURCE

CROSS-REFERENCE TO RELATED APPLICATIONS

This application is a continuation of International Patent Application No. PCT/CN2020/109005, filed on Aug. 13, 2020, the entire contents of which are hereby incorporated by reference.

TECHNICAL FIELD

The present disclosure generally relates to radiation devices, and more particularly, relates to systems and methods for modeling a radiation source of a radiation device.

BACKGROUND

Radiotherapy using a radiation source (e.g., an electron linear accelerator) is a known treatment for various tumors (e.g., nasopharyngeal cancer, breast cancer, or skin cancer). The radiation source may need to provide sufficient and accurate radiation dose to a region of interest (e.g., a tumor) of an object (e.g., a patient) and avoid other regions (e.g., normal organs or tissue) of the object from being radiated as less as possible. In modern radiotherapy practice, a treatment planning system (TPS) may be used to predict a dose distribution in the object to the radiation from the radiation source using a Monte Carlo algorithm. The key to the Monte Carlo algorithm is to construct a virtual source model for modeling the radiation source. However, the current modeling process may need to consider a plurality of virtual source types and need a large amount of measured data, which is complex and time-consuming. Therefore, it is desirable to develop systems and methods for efficiently modeling the radiation source, thereby improving the accuracy of determining the dose distribution in the patient to the radiation from the radiation source.

SUMMARY

According to an aspect of the present disclosure, a system is provided. The system may include at least one storage device including a set of instructions for modeling a radiation source configured to emit radiation of an energy spectrum that includes a plurality of energy levels. The system may also include at least one processor in communication with the storage device. When executing the set of instructions, the at least one processor may be configured to cause the system to perform operations including: obtaining an initial multi-source model of the radiation source, wherein the initial multi-source model includes an initial phase space file that includes information of a plurality of simulated particles of the plurality of energy levels; estimating, based on the initial phase space file, a plurality of component percentage depth-dose (PDD) curves in a phantom, wherein each of the plurality of component PDD curves corresponds to one of the plurality of energy levels; obtaining a measured PDD curve in the phantom corresponding to the radiation of the energy spectrum traversing the phantom; for each of the plurality of energy levels, determining, based on the plurality of component PDD curves and the measured PDD curve, a weight for the each energy level indicating a percentage of simulated particles of the each energy level, among the plurality of simulated particles, present in the radiation; and determining a target multi-source model of the radiation source corresponding to the energy spectrum based at least in part on the initial multi-source model and the weights.

In some embodiments, the initial phase space file may include a group of initial weights each of which corresponds to one of the plurality of energy levels. To determine a weight for each of the plurality of energy levels, the at least one processor may further be configured to cause the system to perform operations including determining, based on the plurality of component PDD curves, a combined PDD curve by adjusting at least one of the group of initial weights until a first difference between the combined PDD curve and the measured PDD curve is below a first threshold; and determining, based on the adjusted group of weights, the weight for each of the plurality of energy levels.

In some embodiments, the radiation source may include a primary source and an electron applicator. The radiation may include primary electrons and secondary electrons. The primary electrons may be generated by the primary source. The primary electrons may include a first portion that exits the radiation source without being scattered and a second portion. The secondary electrons may be generated by the second portion of the primary electrons impinging on the electron applicator.

In some embodiments, a first portion of the simulated particles may correspond to the first portion of primary electrons.

In some embodiments, the radiation may further include photons. A second portion of the simulated particles may correspond to the photons.

In some embodiments, the photons may be generated by the primary source.

In some embodiments, the initial multi-source model of the radiation source may include a primary virtual source corresponding to the first portion of the simulated particles and the second portion of the simulated particles for simulating the primary source.

In some embodiments, the primary virtual source may be a point source.

In some embodiments, the initial phase space file may include positions of the first portion of the simulated particles and directions of the first portion of the simulated particles.

In some embodiments, the positions of the first portion of the simulated particles or the directions of the first portion of the simulated particles may be determined by a direct sampling based on a first distribution function. A particle flux distribution of the first portion of the simulated particles on a plane perpendicular to an axis of the primary virtual source may conform to the first distribution function.

In some embodiments, the first distribution function may be a first Gaussian function.

In some embodiments, a third portion of the simulated particles may correspond to the secondary electrons, and the initial multi-source model of the radiation source may include a secondary virtual source corresponding to the third portion of the simulated particles for simulating the electron applicator.

In some embodiments, the secondary virtual source may include at least one of a second point source or a plane source.

In some embodiments, the initial phase space file may include positions of the third portion of the simulated particles and directions of the third portion of the simulated particles.

In some embodiments, the third portion of simulated particles may include a first sub-portion of simulated particles corresponding to the second point source and a second sub-portion of simulated particles corresponding to the plane source. Positions of the first sub-portion of simulated particles or directions of the first sub-portion of simulated particles may be determined by a second direct sampling based on a second distribution function. A particle flux distribution of the first sub-portion of simulated particles on a second plane perpendicular to the axis of the primary virtual source may conform to the second distribution function. Positions of the second sub-portion of simulated particles or directions of the second sub-portion of simulated particles may be determined by a third direct sampling based on a third distribution function. A flux distribution of the second sub-portion of simulated particles on a third plane perpendicular to the axis of the primary virtual source may conform to the third distribution.

In some embodiments, the second distribution function may be a second Gaussian function, and the third distribution function may be a uniform distribution function.

In some embodiments, the at least one processor may be further configured to cause the system to perform the operations including obtaining a measured off-axis ratio (OAR) curve corresponding to the radiation of the energy spectrum traversing the phantom; determining a simulated OAR curve in the phantom based on parameters of the primary virtual source of the initial multi-source model and the initial phase space file; adjusting the parameters of the primary virtual source until a second difference between a penumbra region of the simulated OAR curve and a penumbra region of the measured OAR curve is below a second threshold; and determining the target multi-source model of the radiation source based further on the adjusted parameters of the primary virtual source.

In some embodiments, the parameters of the primary virtual source may include at least one of a size of the primary virtual source, a vertical position of the primary virtual source along the axis of the primary virtual source, or a particle flux distribution of the primary virtual source.

In some embodiments, the primary source may be configured to be operably coupled to one of a plurality of second electron applicators. The at least one processor is further configured to cause the system to perform the operations including for each of the plurality of second electron applicators, obtaining an output coefficient corresponding to the second electron applicator; determining a simulated output coefficient corresponding to the second electron applicator based on structural parameters of the second electron applicator; and determining a correction coefficient for the second electron applicator based on the output coefficient and the simulated output coefficient.

In some embodiments, to determine a weight for each of the plurality of energy levels, the at least one processor is further configured to cause the system to perform the operations including receiving a user input relating to the weight for the energy level; and determining the weight for the energy level based at least in part on the user input.

In some embodiments, the radiation source may be a linear accelerator.

In some embodiments, the at least one processor may be further configured to direct the system to perform operations including estimating an average energy level of the photons based on the energy spectrum; determining a measured average energy level of the photons based on the measured PDD curve;
determining, based on the estimated average energy level and the measured energy level, a weight for the photons; and determining the target multi-source model based further on the weight for the photons.

In some embodiments, the electron applicator may include at least an upper part, a middle part, and a lower part. The second point source may correspond to the upper part and the middle part of the electron applicator, and the plane source may correspond to the lower part of the electron applicator.

In some embodiments, the radiation source may include a collimation component. The initial multi-source model of the radiation source may further include a third virtual source corresponding to the collimation component.

In some embodiments, the third virtual source may be a line source.

According to another aspect of the present disclosure, a system is provided. The system may include at least one storage device storing a set of instructions for determining a dose distribution in an object subject to radiation of an energy spectrum from a radiation source. The radiation source may include a primary source and an electron applicator. The system may also include at least one processor in communication with the storage device. When executing the set of instructions, the at least one processor may be configured to cause the system to perform operations including obtaining structural parameters of the electron applicator; obtaining a target multi-source model of the radiation source corresponding to the energy spectrum; determining, based on the target multi-source model and the structural parameters of the electron applicator, a phase space file including information of a plurality of simulated particles corresponding to the radiation; obtaining a transport model of the radiation of the energy spectrum traversing the object; and determining the dose distribution in the object based on the phase space file and the transport model.

In some embodiments, the target multi-source model may include a primary virtual source corresponding to the primary source. The primary virtual source may be a first point source.

In some embodiments, the target multi-source model of the radiation source may include a secondary virtual source corresponding to the electron applicator. The secondary virtual source may include a second point source and a plane source.

In some embodiments, the electron applicator may include at least an upper part, a middle part, and a lower part. The second point source may correspond to the upper part and the middle part of the electron applicator. The plane source may correspond to the lower part of the electron applicator.

In some embodiments, the radiation may include primary electrons, photons, and secondary electrons. The primary electrons and the photons may be generated by the primary source. The primary electrons may include a first portion that exit the radiation source without may be scattered and a second portion. The secondary electrons may be generated by the second portion of the primary electrons impinging on the electron applicator.

In some embodiments, a first portion of the simulated particles may correspond to the first portion of the primary electrons. A second portion of the simulated particles may correspond to the photons. A third portion of the simulated particles may correspond to the secondary electrons.

In some embodiments, the phase space file may include at least one of a position, a direction, or an energy, of each of the plurality of simulated particles.

In some embodiments, the position, the direction, or the energy, of the each of the plurality of simulated particles may be determined based on a direct sampling.

In some embodiments, for each of the first portion of the simulated particles, the at least one processor may be further configured to cause the system to perform operations including determining a position of the simulated particle or a direction of the simulated particle by a first direct sampling based on a first distribution function, wherein a particle flux distribution of the first portion of the simulated particles on a plane perpendicular to an axis of the primary virtual source conforming to the first distribution function; and determining a particle energy of the simulated particle by a second direct sampling of the energy spectrum based on the target multi-source model.

In some embodiments, the first distribution function may be a first Gaussian function.

In some embodiments, the second portion of the simulated particles may include a first sub-portion of simulated particles corresponding to the second point source and a second sub-portion of simulated particles corresponding to the plane source.

In some embodiments, for each of the first sub-portion of simulated particles, the at least one processor may be further configured to cause the system to perform the operations including determining a position of the simulated particle or a direction of the simulated particle by a third direct sampling based on a second distribution function; and determining a particle energy of the simulated particle by a fourth direct sampling of the energy spectrum based on the target multi-source model. A particle flux distribution of the first sub-portion of simulated particles on a second plane perpendicular to the axis of the primary virtual source may conform to the second distribution function.

In some embodiments, the second distribution function may be a second Gaussian function.

In some embodiments, for each of the second sub-portion of simulated particles, the at least one processor may be further configured to cause the system to perform operations including determining a position of the simulated particle or a direction of the simulated particle by a fifth direct sampling based on a third distribution function; and determining a particle energy of the simulated particle by a sixth direct sampling of the energy spectrum based on the target multi-source model. A particle flux distribution of the second sub-portion of simulated particles on a plane perpendicular to the axis of the primary virtual source may conform to the third distribution function.

In some embodiments, at least one of the third distribution function may be a uniform distribution function.

In some embodiments, the radiation source may include a collimation component. The target multi-source model of the radiation source may further include a third virtual source corresponding to the collimation component, the third virtual source may be a line source.

In some embodiments, the radiation source may be a linear accelerator.

According to another aspect of the present disclosure, a method for modeling a radiation source configured to emit radiation of an energy spectrum that includes a plurality of energy levels is provided. The method may be implemented on a computing device including at least one processor and at least one storage device. The method may include obtaining an initial multi-source model of the radiation source, wherein the initial multi-source model includes an initial phase space file that includes information of a plurality of simulated particles of the plurality of energy levels; estimating, based on the initial phase space file, a plurality of component percentage depth-dose (PDD) curves in a phantom, wherein each of the plurality of component PDD curves corresponds to one of the plurality of energy levels; obtaining a measured PDD curve in the phantom corresponding to the radiation of the energy spectrum traversing the phantom; for each of the plurality of energy levels, determining, based on the plurality of component PDD curves and the measured PDD curve, a weight for the each energy level indicating a percentage of simulated particles of the each energy level, among the plurality of simulated particles, present in the radiation; and determining a target multi-source model of the radiation source corresponding to the energy spectrum based at least in part on the initial multi-source model and the weights.

According to another aspect of the present disclosure, a method for determining a dose distribution in an object subject to radiation of an energy spectrum from a radiation source is provided. The radiation source may include a primary source and an electron applicator. The method may be implemented on a computing device including at least one processor and at least one storage device. The method may include obtaining structural parameters of the electron applicator; obtaining a target multi-source model of the radiation source corresponding to the energy spectrum; determining, based on the target multi-source model and the structural parameters of the electron applicator, a phase space file including information of a plurality of simulated particles corresponding to the radiation; obtaining a transport model of the radiation of the energy spectrum traversing the object; and determining the dose distribution in the object based on the phase space file and the transport model.

According to yet another aspect of the present disclosure, a system for modeling a radiation source configured to emit radiation of an energy spectrum that includes a plurality of energy levels is provided. The system may include an obtaining module, an estimation module, and a determination module. The obtaining module may be configured to obtain an initial multi-source model of the radiation source and a measured PDD curve in the phantom corresponding to the radiation of the energy spectrum traversing the phantom. The initial multi-source model may include an initial phase space file that includes information of a plurality of simulated particles of the plurality of energy levels. The estimation module may be configured to estimate, based on the initial phase space file, a plurality of component percentage depth-dose (PDD) curves in a phantom. Each of the plurality of component PDD curves may correspond to one of the plurality of energy levels. The determination module may be configured to for each of the plurality of energy levels, determine, based on the plurality of component PDD curves and the measured PDD curve, a weight for the each energy level indicating a percentage of simulated particles of the each energy level, among the plurality of simulated particles, present in the radiation. The determination module may also be configured to determine a target multi-source model of the radiation source corresponding to the energy spectrum based at least in part on the initial multi-source model and the weights.

According to yet another aspect of the present disclosure, a system for determining a dose distribution in an object subject to radiation of an energy spectrum from a radiation source is provided. The radiation source may include a primary source and an electron applicator. The system may include an obtaining module and a determination module. The obtaining module may be configured to obtain structural parameters of the electron applicator, obtain a target multi-source model of the radiation source corresponding to the energy spectrum, and obtain a transport model of the radiation of the energy spectrum traversing the object. The determination module may be configured to determine, based on the target multi-source model and the structural parameters of the electron applicator, a phase space file including information of a plurality of simulated particles corresponding to the radiation. The determination module may also be configured to determine the dose distribution in the object based on the phase space file and the transport model.

According to yet another aspect of the present disclosure, a non-transitory computer readable medium is provided, comprising at least one set of instructions, wherein when executed by at least one processor of a computing device, the at least one set of instructions direct the at least one processor to perform a method for modeling a radiation source configured to emit radiation of an energy spectrum that includes a plurality of energy levels. The method may include obtaining an initial multi-source model of the radiation source, wherein the initial multi-source model includes an initial phase space file that includes information of a plurality of simulated particles of the plurality of energy levels; estimating, based on the initial phase space file, a plurality of component percentage depth-dose (PDD) curves in a phantom, wherein each of the plurality of component PDD curves corresponds to one of the plurality of energy levels; obtaining a measured PDD curve in the phantom corresponding to the radiation of the energy spectrum traversing the phantom; for each of the plurality of energy levels, determining, based on the plurality of component PDD curves and the measured PDD curve, a weight for the each energy level indicating a percentage of simulated particles of the each energy level, among the plurality of simulated particles, present in the radiation; and determining a target multi-source model of the radiation source corresponding to the energy spectrum based at least in part on the initial multi-source model and the weights.

According to yet another aspect of the present disclosure, a non-transitory computer readable medium is provided, comprising at least one set of instructions, wherein when executed by at least one processor of a computing device, the at least one set of instructions direct the at least one processor to perform a method for determining a dose distribution in an object subject to radiation of an energy spectrum from a radiation source. The method may include obtaining structural parameters of the electron applicator; obtaining a target multi-source model of the radiation source corresponding to the energy spectrum; determining, based on the target multi-source model and the structural parameters of the electron applicator, a phase space file including information of a plurality of simulated particles corresponding to the radiation; obtaining a transport model of the radiation of the energy spectrum traversing the object; and determining the dose distribution in the object based on the phase space file and the transport model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for modeling a radiation source according to some embodiments of the present disclosure;

FIG. 8 is a flowchart illustrating an exemplary process for determining a weight from each of a plurality of energy levels of an energy spectrum of a radiation source according to some embodiments of the present disclosure;

FIG. 11 is a flowchart illustrating an exemplary process for determining a correction coefficient corresponding to an electron applicator according to some embodiments of the present disclosure;

FIG. 12 is a flowchart illustrating an exemplary process for determining a dose distribution in an object according to some embodiments of the present disclosure;

FIG. 13 is a flowchart illustrating an exemplary process for determining a phase space file of a target multi-source model according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Figure 2:
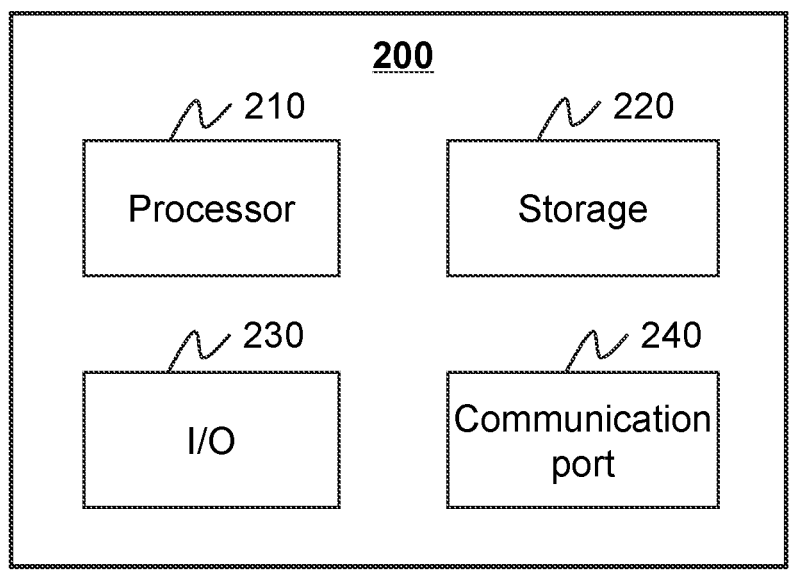
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "modality" as used herein broadly refers to an imaging or treatment method or technology that gathers, generates, processes, and/or analyzes imaging information of a subject or treatments the subject. The subject may include a biological object and/or a non-biological object. The biological subject may be a human being, an animal, a plant, or a portion thereof (e.g., a cell, a tissue, an organ, etc.). In some embodiments, the subject may be a man-made composition of organic and/or inorganic matters that are with or without life. The term "object" or "subject" are used interchangeably in the present disclosure.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "region," "location," and "area" in the present disclosure may refer to a location of an anatomical structure shown in the image or an actual location of the anatomical structure existing in or on a target subject's body, since the image may indicate the actual location of a certain anatomical structure existing in or on the target subject's body. In some embodiments, an image of an object may be referred to as the object for brevity. Segmentation of an image of an object may be referred to as segmentation of the object. For example, segmentation of an organ refers to segmentation of a region corresponding to the organ in an image.

The present disclosure provides mechanisms (which can include methods, systems, a computer-readable medium, etc.) for modeling a radiation source. The methods may include obtaining an initial multi-source model of a radiation source. The radiation source may be configured to emit radiation of an energy spectrum that includes a plurality of energy levels. The initial multi-source model may include an initial phase space file that includes information of a plurality of simulated particles of the plurality of energy levels. The methods may also include determining a weight for each of the plurality of energy levels based on a plurality of estimated component percentage depth-dose (PDD) curves in a phantom corresponding to the plurality of energy levels and a measured PDD curve in the phantom corresponding to the radiation of the energy spectrum traversing the phantom. The methods may also include determining parameters of a primary virtual source of the initial multi-source model based on a simulated off-axis ratio (OAR) curve and a measured OAR curve corresponding to the radiation of the energy spectrum traversing the phantom. The methods may also include determining a correction coefficient for an electron applicator operably coupled to the primary source. The methods may further include determining a target multi-source model based on the initial multi-source model, the weights, the parameters of the primary virtual source, and the correction coefficient.

The present disclosure also provides mechanisms (which can include methods, systems, a computer-readable medium, etc.) for determining a dose distribution in an object subject to radiation of an energy spectrum from a radiation source. The methods may include obtaining structural parameters of an electron applicator of the radiation source, a target multi-source model of the radiation source corresponding to the energy spectrum, and a transport model of the radiation of the energy spectrum traversing an object. The methods may also include determining, based on the target multi-source model and the structural parameters of the electron applicator, a phase space file including information of a plurality of simulated particles corresponding to radiation of the radiation source. The methods may further include determining the dose distribution in the object based on the phase space file and the transport model.

According to some embodiments of the present disclosure, the target multi-source model may include a primary virtual source for simulating the primary source and a secondary virtual source for simulating the electron applicator, which reduces a count of virtual sources in modeling a radiation source. During the modeling process, only parameters of the primary virtual source need to be adjusted and parameters of the secondary virtual source may be determined based on structural parameters of the corresponding electron applicator, thereby reducing the complexity of the modeling process. In some embodiments, an energy spectrum corresponding to a specific energy setting of the radiation source may be estimated based on a reference electron applicator; the estimated energy spectrum may be applied in determining a multi-source model of the radiation source for that specific energy setting while the radiation source includes one of various electron applicators other than the reference electron applicator, thereby obviating the need to repeatedly estimate the energy spectrum for a same energy setting of the radiation source for each of different electron applicators, which in turn may reduce the computational load of the modeling process and improve the efficiency of the modeling process. In some embodiments, instead of pre-determining and storing in a storage device a phase space file including information of simulated scattered particles for each of various configurations of the radiation source, e.g., various electron applicators, positions and directions of a plurality of simulated particles may be determined based on a direct sampling during the modeling process, thereby reducing the storage space used for storing the phase space file of the target multi-source model. Further, the target multi-source model of the radiation source may be applied to determine a dose distribution in an object subject to radiation of the energy spectrum from the radiation source, thereby improving the efficiency and the accuracy of the dose distribution estimate.

Figure 1:
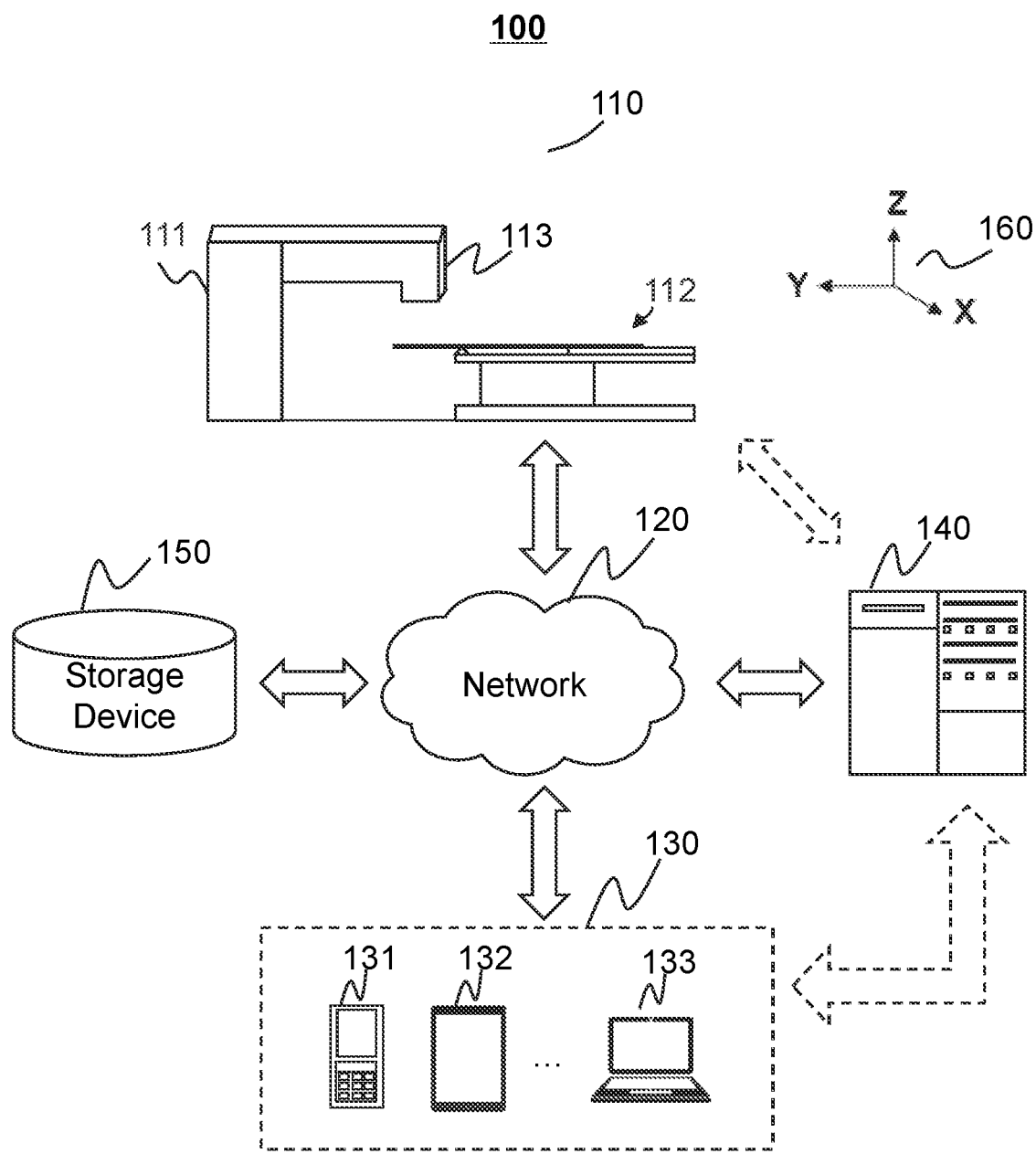
FIG. 1 is a schematic diagram illustrating an exemplary medical system according to some embodiments of the present disclosure.

FIG. 1 is a schematic diagram illustrating an exemplary medical system according to some embodiments of the present disclosure. The medical system may be used for non-invasive imaging and/or treatment using a radiation source, such as for disease diagnosis, treatment, or research purposes. In some embodiments, the medical system may include a single modality system or a multi-modality system. The single modality system may include, for example, a radiotherapy (RT) device, an X-ray imaging system, a computed tomography (CT) system, a single photon emission computed tomography (SPECT) system, a digital radiography (DR) system, or the like, or any combination thereof. The multi-modality system may include, for example, an image-guided radiotherapy (IGRT) system (e.g., a CT guided RT system, and a magnetic resonance imaging (MRI) guided RT system), an X-ray imaging-MRI (X-ray-MRI) system, a SPECT-MRI system, a CT-positron emission tomography (CT-PET) system, etc It should be noted that the medical system described below is merely provided for illustration purposes, and not intended to limit the scope of the present disclosure. The following descriptions are provided with reference to the medical system illustrated in FIG. 1 being an RT system. It is understood that this is for illustration purposes and not intended to be limiting.

As shown in FIG. 1, the medical system 100 may include a medical device 110, a network 120, one or more terminals 130, a processing device 140, and a storage device 150. In some embodiments, two or more components of the medical system 100 may be connected to and/or communicate with each other via a wireless connection (e.g., the network 120), a wired connection, or a combination thereof. The connection between the components of the medical system 100 may be variable. Merely by way of example, the medical device 110 may be connected to the processing device 140 through the network 120 or directly. As a further example, the storage device 150 may be connected to the processing device 140 through the network 120 or connected to the processing device 140 directly.

The medical device 110 may be configured to deliver a radiotherapy treatment to an object (e.g., a patient or a portion thereof). For example, the medical device 110 may be a treatment device including a gantry 111, a table 112, a treatment head 113, etc. The gantry 111 may be configured to provide support for other components (e.g., the treatment head 113) of the medical device 110. The table 112 may be configured to support and move the object to a desired position (e.g., a treatment position under the treatment head 113 for treatment). The treatment head 113 may include a radiation source configured to emit therapeutic radiation toward the object for treatment. For illustration purposes, the radiation source of the treatment head 113 may be a linear accelerator, which is not intended to be limiting. More descriptions regarding the treatment head 113 may be found elsewhere in the present disclosure (e.g., FIG. 4 and the description thereof). In some embodiments, the medical device 110 may include a drum instead of the gantry 111 to provide support for the treatment head 113.

The network 120 may include any suitable network that can facilitate the exchange of information and/or data for the medical system 100. In some embodiments, one or more components of the medical system 100 (e.g., the medical device 110, the processing device 140, the storage device 150, the terminal(s) 130) may communicate information and/or data with one or more other components of the medical system 100 via the network 120. For example, the processing device 140 may obtain image data from the medical device 110 via the network 120. As another example, the processing device 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the medical system 100 may be connected to the network 120 to exchange data and/or information.

The terminal(s) 130 may be connected to and/or communicate with the medical device 110, the processing device 140, and/or the storage device 150. For example, the terminal(s) 130 may obtain a dose distribution of an object from the processing device 140. As another example, the terminal(s) 130 may enable user interactions with the medical system 100. In some embodiments, the terminal(s) 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 130 may include an input device, an output device, etc. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to the processing device 140 via, for example, a bus, for further processing. Other types of input device may include a cursor control device, such as a mouse, a trackball, or cursor direction keys, etc. The output device may include a display, a speaker, a printer, or the like, or a combination thereof. In some embodiments, the terminal(s) 130 may be part of the processing device 140.

The processing device 140 may process data and/or information obtained from the medical device 110, the storage device 150, the terminal(s) 130, or other components of the medical system 100. For example, the processing device 140 may determine a target multi-source model of a radiation source corresponding to an energy spectrum based on an initial multi-source model, a plurality of component PDD curves in a phantom, and a measured PDD curve in the phantom corresponding to the radiation of the energy spectrum traversing the phantom. As another example, the processing device 140 may determine, based on the target multi-source model and structural parameters of an electron applicator operably coupled to the radiation source, a dose distribution in an object subject to radiation of the energy spectrum from the radiation source. In some embodiments, the processing device 140 may be a single server or a server group. The server group may be centralized or distributed. In some embodiments, the processing device 140 may be local to or remote from the medical system 100. For example, the processing device 140 may access information and/or data from the medical device 110, the storage device 150, and/or the terminal(s) 130 via the network 120. As another example, the processing device 140 may be directly connected to the medical device 110, the terminal(s) 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, and inter-cloud, a multi-cloud, or the like, or a combination thereof. In some embodiments, the processing device 140 may be implemented by a computing device 200 having one or more components as described in connection with FIG. 2.

The storage device 150 may store data, instructions, and/or any other information. In some embodiments, the storage device 150 may store data obtained from the processing device 140, the terminal(s) 130, and/or the storage device 150. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage device may include a magnetic disk, an optical disk, a solid-state drive, etc. Exemplary removable storage device may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the medical system 100 (e.g., the processing device 140, the terminal(s) 130). One or more components of the medical system 100 may access the data or instructions stored in the storage device 150 via the network 120. In some embodiments, the storage device 150 may be part of the processing device 140.

In some embodiments, a three-dimensional coordinate system 160 may be used in the medical system 100 as illustrated in FIG. 1. A first axis may be parallel to the lateral direction of the couch (e.g., the X-direction as shown in FIG. 1). A second axis may be parallel to the longitudinal direction of the couch (e.g., the Y-direction as shown in FIG. 1). A third axis may be parallel to a vertical direction of the couch (e.g., the Z direction as shown in FIG. 1). The origin of the three-dimensional coordinate system 160 may be any point in the space. In some embodiments, the origin of the three-dimensional coordinate system 160 may be determined by an operator. In some embodiments, the origin of the three-dimensional coordinate system 160 may be determined by the medical system 100. In some embodiments, the position of the one or more portions of the object (e.g., a target volume) may be described using the 3D coordinate system 160. In some embodiments, the position of different portions of the treatment head 113 may be described using the 3D coordinate system 160.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage device including cloud computing platforms, such as public cloud, private cloud, community, and hybrid clouds, etc. However, those variations and modifications do not depart the scope of the present disclosure.

FIG. 2 is a schematic diagram illustrating exemplary hardware and/or software components of an exemplary computing device on which the processing device 140 may be implemented according to some embodiments of the present disclosure. As illustrated in FIG. 2, a computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the medical device 110, the terminals 130, the storage device 150, and/or any other component of the medical system 100. In some embodiments, the processor 210 may include one or more hardware processors, such as a microcontroller, a microprocessor, a reduced instruction set computer (RISC), application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, and thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical device 110, the terminals 130, the storage device 150, and/or any other component of the medical system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 for modeling a radiation source configured to emit radiation of an energy spectrum that includes a plurality of energy levels and/or determining a dose distribution in an object subject to radiation of the energy spectrum from the radiation source.

The I/O 230 may input and/or output signals, data, information, etc. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the medical device 110, the terminals 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
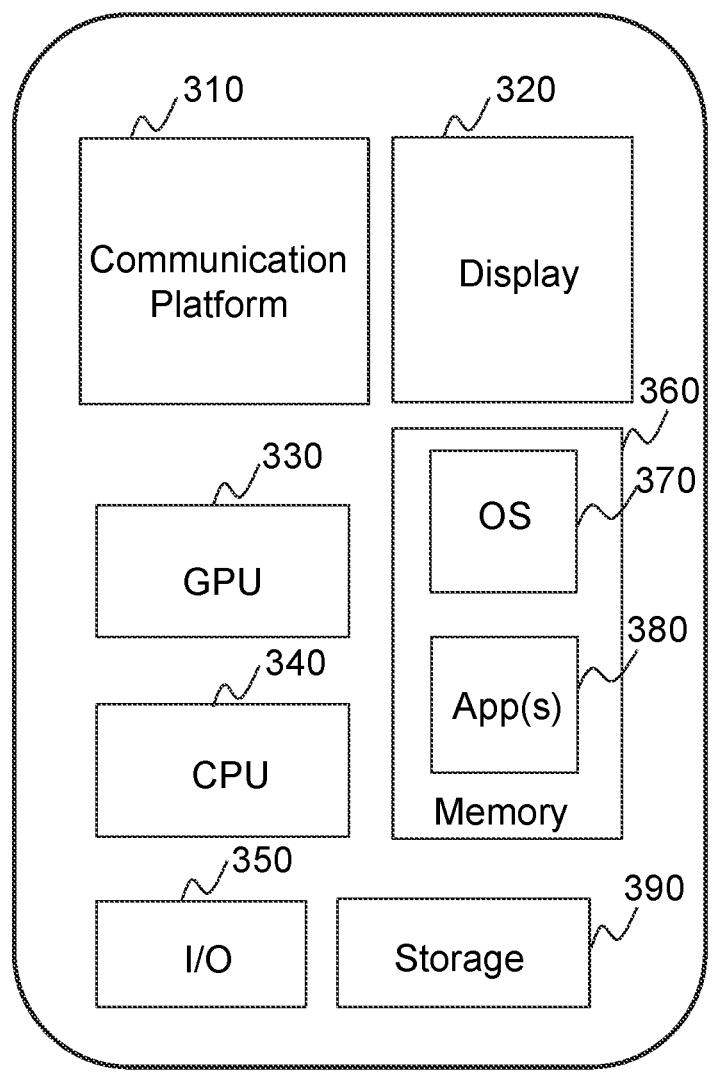
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, one or more components (e.g., the terminal(s) 130 and/or the processing device 140) of the medical system 100 may be implemented on the mobile device 300.

As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™ Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the medical system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
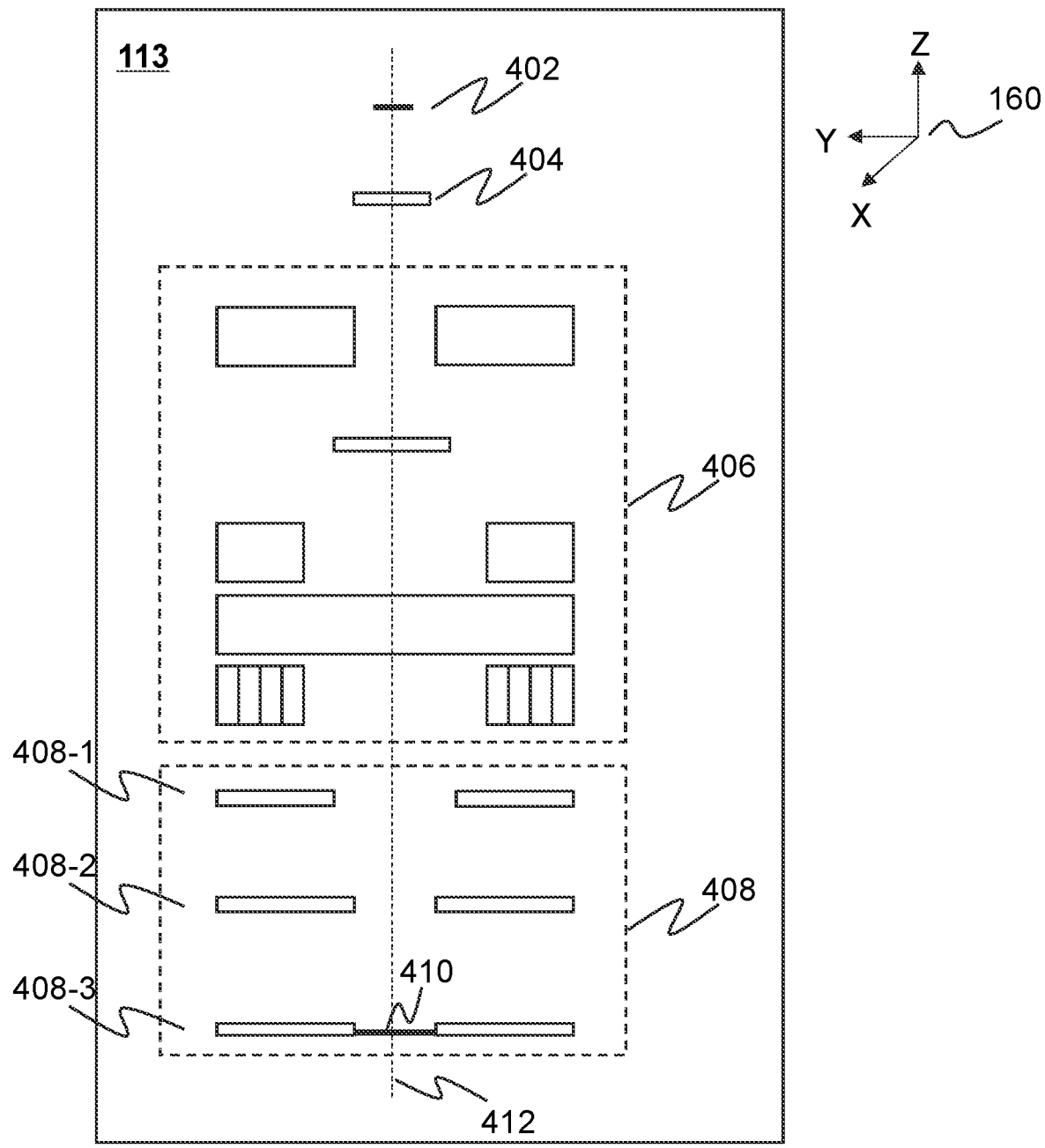
FIG. 4 is a schematic diagram illustrating an exemplary radiation source of the treatment head 113 according to some embodiments of the present disclosure.

FIG. 4 is a schematic diagram illustrating an exemplary radiation source of the treatment head 113 according to some embodiments of the present disclosure. The radiation source of the treatment head 113 may be an electron linear accelerator configured to generate and emit electron radiation toward an object for treatment. As shown in FIG. 4, the radiation source may include a generator 402, a scattering foil 404, a collimation component (or a beam limiting component) 406, a plurality of electron applicators 408, or the like, or any combination thereof. The radiation source may be operable for a radiotherapeutic treatment when one of the plurality of electron applicators 408 is mounted.

The generator 402 may be configured to generate an accelerated electron beam (also referred to as a radiation beam) for the therapeutic radiation of the object. For example, the generator 402 may heat a tungsten wire in the generator 402 to generate electrons. The generator 402 may generate the radiation beam by further accelerating the generated electrons. The radiation beam may exit from the generator 402 from an exit window located at the bottom of the generator 402.

In some embodiments, the radiation beam produced by the generator 402 may be a narrow beam with a relatively small scattering angle such as to be considered corresponding to a single energy level. The scattering foil 404 may be configured to broaden the radiation beam according to the scattering nature of electrons. On such occasions, the effect of the interaction between the generator 402 and the scattering foil 404 may be accounted for using a primary source. It should be noted that the primary source may be an assumed source according to the structures and layout of various components including the generator 402, the scattering foil 404, the scattering nature of electrons, etc. In some embodiments, the generator 402 or the scattering foil 404 may be designated as the primary source for brevity.

The collimation component 406 may be configured to shape the radiation beam. For example, the broadened radiation beam may pass through the collimation component 406 to form a beam with a specific shape (e.g., a cone beam). In some embodiments, the collimation component 406 may include a primary collimator, a secondary scattering foil, a secondary collimator, a multi-leaf collimator (MLC), or the like, or any combination thereof. In some embodiments, a size of a radiation field of the collimation component 406 may be adjusted automatically according to an electron applicator 408 operably coupled to the primary source. That is, a specific electron applicator 408 may correspond to a specific size of the radiation field of the collimation component 406. As used herein, a radiation field of the collimation component 406 refers to an end opening (e.g., an opening in a bottom end) of the collimation component 406 through which a radiation beam may exit from the collimation component 406.

Each of the plurality of electron applicators 408 may be configured to reduce electron leakage of the radiation beam and reshape the radiation beam. For example, the beam with a specific shape exiting from the collimation component 406 may pass through the electron applicator 408 to form radiation, or referred to as a radiation beam, of a certain shape, e.g., a square, a circle. As used herein, the shape of radiation or a radiation beam refers to the shape of a cross section of the radiation beam (constituting the radiation). In some embodiments, the certain shape of the radiation may be consistent with the shape (e.g., a circle, or a square) of an end opening (e.g., an opening in a bottom) of the electron applicator 408 through which a radiation beam may exit the electron applicator 408. In some embodiments, the plurality of electron applicators 408 may facilitate the formation of different radiation beams. For instance, the size of the end opening of an electron applicator may be 6×6 cm$^2$, 10×10 cm$^2$, 15×15 cm$^2$, 20×20 cm$^2$, 25×25 cm$^2$, etc. For brevity, an electron applicator whose end opening is of a specific size may be referred to as an electron applicator of the specific size. For instance, an electron applicator whose end opening is of 10×10 cm$^2$ may be referred to as an electron applicator of 10×10 cm$^2$. In some embodiments, each of the plurality of electron applicators 408 may include a multi-layer structure (e.g., a two-layer structure, a three-layer structure, or a four-layer structure). Merely by way of example, an electron applicator 408 may include a first part (also referred to as an upper part) 408-1, a second part (also referred to as a middle part) 408-2, and a third part (also referred to as a lower part) 408-3 as shown in FIG. 4.

In some embodiments, a radiation beam generated by the primary source may include primary electrons and primary photons. The primary electrons may include a first portion that are not scattered within the radiation source and a second portion. The second portion of the primary electrons may impinge on other components (e.g., the collimation component 406, the electron applicator 408, etc.) of the radiation source to generate secondary electrons. The primary photons may include a third portion that does not interact with other components of the radiation source within the radiation source and a fourth portion. The fourth portion of the primary photons may interact with other components (e.g., the collimation component 406, the electron applicator 408, etc.) of the radiation source to generate secondary photons.

The primary electrons and the secondary electrons may be of different energy levels. For example, the primary electrons may have relatively high energies, and the secondary electrons may have relatively low energies. Accordingly, the radiation exiting the radiation source may correspond to an energy spectrum including a plurality of energy levels (e.g., a plurality of electron energy levels). In some embodiments, secondary electrons generated by the second portion of the primary electrons impinging on the collimation component 406 may account for a relatively low percentage among the radiation traversing the object, which may be omitted. In some embodiments, the secondary photons may account for a relatively low percentage among the photon contamination, which may be omitted.

In some embodiments, the radiation source may have an axis 412 perpendicular to an exit of the radiation source as shown in FIG. 4. For example, the axis 412 may pass through a center of the electron applicator 408. As another example, the axis 412 may be parallel to the Z-axis of the coordinate system 160.

In some embodiments, the radiation, after exiting the treatment head 113, may then traverse the object for the radiotherapeutic treatment. The radiation traversing the object may include the first portion of the primary electrons, the secondary electrons, the third portion of the primary photons, and the secondary photons. The third portion of the primary photons and the secondary photons may be regarded as photon contamination during the radiotherapeutic treatment.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the radiation source may further include a block 410 mounted on a bottom of the electron applicator 408 (e.g., attached on the lower part 408-3 of the electron applicator 408 as shown in FIG. 4). The block 410 may be configured to further shape the radiation beam. The block 410 may include an opening to modulate the radiation beam to a size that is smaller than the size of the radiation beam exiting the electron applicator 408. The opening of the block 410 may be of a regular shape (e.g., triangle, hexagon, oval, rectangle, etc.) or an irregular shape. The block may be made of a material that is radiation impermeable including, e.g., lead. In such cases, the radiation exiting the radiation source (and subsequently traversing the object) may include secondary electrons generated by the second portion of the primary electrons impinging on the block 410.

Figure 5A:
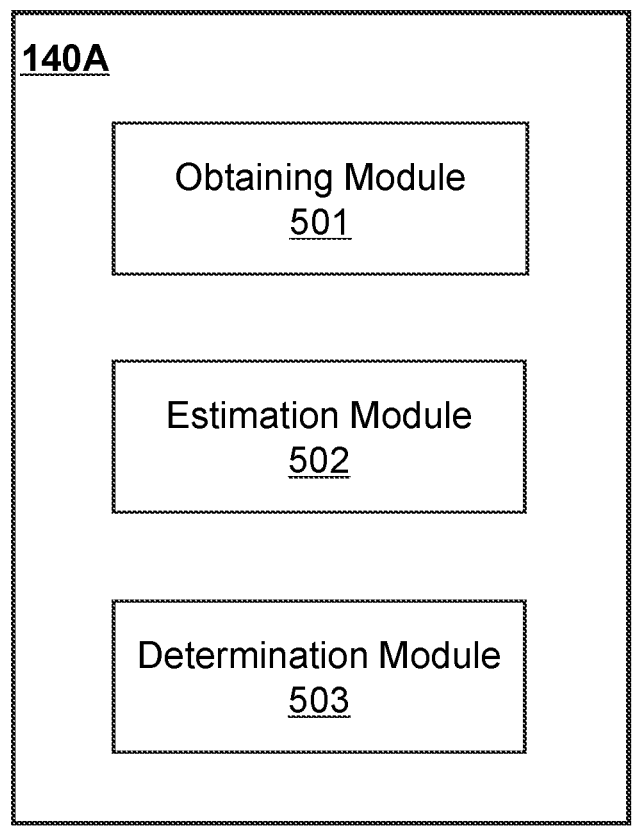
FIG. 5A is a block diagram illustrating an exemplary processing device according to some embodiments of the present disclosure.
Figure 5B:
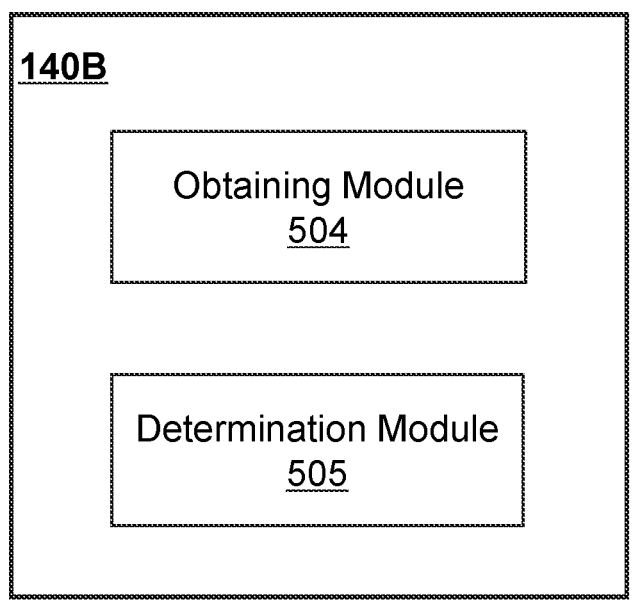
FIG. 5B is a block diagram illustrating an exemplary processing device according to some embodiments of the present disclosure.

FIG. 5A and FIG. 5B are block diagrams illustrating exemplary processing devices according to some embodiments of the present disclosure. In some embodiments, the processing devices 140A and 140B may be embodiments of the processing device 140 as described in connection with FIG. 1. In some embodiments, the processing devices 140A and 140B may be respectively implemented on a processing unit (e.g., the processor 210 illustrated in FIG. 2 or the CPU 340 as illustrated in FIG. 3). Merely by way of example, the processing devices 140A may be implemented on a CPU 340 of a terminal device, and the processing device 140B or the processing device 140A may be implemented on a computing device 200. Alternatively, the processing devices 140A and 140B may be implemented on a same computing device 200 or a same CPU 340. For example, the processing devices 140A and 140B may be implemented on a same computing device 200.

As shown in FIG. 5A, the processing device 140A may include an obtaining module 510, an estimation module 502, and a determination module 503.

The obtaining module 501 may be configured to obtain information/data from one or more components of the medical system 100. For example, the obtaining module 501 may obtain an initial multi-source model of a radiation source with a specific energy setting. The radiation source may correspond to an energy spectrum including a plurality of energy levels. The initial multi-source model may include an initial phase space file. The multi-source model may include a primary virtual source and a secondary virtual source. As another example, the obtaining module 501 may obtain measured data relating to radiation of the energy spectrum. For instance, the measured data may include a measured PDD curve and/or a measured OAR curve in a phantom corresponding to the radiation of the energy spectrum traversing the phantom, an output coefficient corresponding to each of a plurality of electron applicators, etc. More descriptions regarding the obtaining of the initial multi-source model and the measured data may be found elsewhere in the present disclosure (e.g., operations 610, 820, 1010, 1110, and the descriptions thereof).

The estimation module 502 may be configured to determine estimated data relating to the radiation of the energy spectrum. For example, the estimation module 502 may estimate a plurality of PDD curves in a phantom corresponding to the plurality of energy levels of the energy spectrum based on the initial phase space file. As another example, the estimation module 502 may determine a simulated OAR curve in the phantom based on initial parameters of the primary virtual source and the initial phase space file. As further another example, the estimation module 502 may determine a simulated output coefficient corresponding to each of the plurality of electron applicators based on structural parameters of the electron intraoral cone and the energy spectrum. More descriptions regarding the determination of the estimated data may be found elsewhere in the present disclosure (e.g., operations 810, 1020, 1120, and the descriptions thereof).

The determination module 503 may be configured to determine a target multi-source model. For example, the determination module 503 may determine a weight for each of the plurality of energy levels. As another example, the determination module 503 may determine a weight for photons. Further, the determination module 503 may determine the energy spectrum based on the weights for the plurality of energy levels and the weight for the photons. As a further example, the determination module 503 may determine parameters of the primary virtual source of the initial multi-source model. As further another example, the determination module 503 may determine a correction coefficient for an electron intraoral cone operably coupled to a primary source of the radiation source. Further, the determination module 503 may determine the target multi-source model of the radiation source corresponding to the energy spectrum based at least in part on the initial multi-source model, the weights, the parameters of the primary virtual source, and the correction coefficient. More descriptions regarding the determination of the weights, the parameters of the primary virtual source, the correction coefficient, and/or the target multi-source model may be found elsewhere in the present disclosure (e.g., operations 620-650, 830-840, 1030-1060, 1130 and the descriptions thereof).

As shown in FIG. 5B, the processing device 140B may include an obtaining module 504, and a determination module 505.

The obtaining module 504 may be configured to obtain information/data associated a dose distribution determination process of an object. For example, the obtaining module 501 may obtain a target multi-source model of a radiation source with a specific energy setting. The obtaining module 504 may obtain structural parameters of an electron applicator of the radiation source. As another example, the obtaining module 504 may obtain a transport model from any storage device.

The determination module 505 may be configured to determine a dose distribution in the object. For example, the determination module 505 may input the structural parameters of the electron applicator into the target multi-source model, and then a phase space file may be determined. The phase space file may include information of a plurality of simulated particles corresponding to radiation of the radiation source. The determination module 505 may determine the dose distribution in the object based on the phase space file and the transport model.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. Each of the modules described above may be a hardware circuit that is designed to perform certain actions, e.g., according to a set of instructions stored in one or more storage media, and/or any combination of the hardware circuit and the one or more storage media.

In some embodiments, the processing device 140A and the processing device 140B may share two or more of the modules, and any one of the modules may be divided into two or more units. For example, the processing device 140A and the processing device 140B may share a same obtaining module (i.e., the obtaining module 501 and the obtaining module 504 may be a same obtaining module). In some embodiments, the processing device 140A and the processing device 140B may include one or more additional modules, such as a storage module (not shown) for storing data. In some embodiments, the processing device 140A and the processing device 140B may be integrated into one processing device 140.

FIG. 6 is a flowchart illustrating an exemplary process for modeling a radiation source according to some embodiments of the present disclosure. In some embodiments, process 600 may be implemented as a set of instructions (e.g., an application) stored in the storage device 150, storage 220, or storage 390. The processing device 140A, the processor 210, and/or the CPU 340 may execute the set of instructions, and when executing the instructions, the processing device 140A, the processor 210, and/or the CPU 340 may be configured to perform the process 600. The operations of the illustrated process presented below are intended to be illustrative. In some embodiments, the process 600 may be accomplished with one or more additional operations not described, and/or without one or more of the operations discussed. Additionally, the order of the operations of the process 600 illustrated in FIG. 6 and described below is not intended to be limiting. For illustration purposes, the process 600 may be described in connection with the radiation source as illustrated in FIG. 4, which is not intended to be limiting.

In some occasions, due to factors such as production accuracy, assembly process, temperature, humidity, etc., dose distributions of a plurality of radiation sources (e.g., linear accelerators) of a same type even by a same manufacturer may be inconsistent to some extent. A radiation source may need to be modeled specifically. A radiation source can produce electron beams under different selectable energy settings (e.g., 8 MeV, 10 MeV, or 12 MeV). Traditionally, the modeling of a radiation source for a specific energy setting needs to consider different electron applicators of the radiation source. That is, an energy spectrum of radiation under a specific energy setting of a radiation source may be determined for each of the different electron applicators, respectively, during the modeling of the radiation source, which is complex and time-consuming. In some embodiments, the process 600 may be performed for modeling the radiation source for a specific selectable energy setting efficiently. For illustration purposes, the modeling process is described with respect to a radiation source that does not include a block.

In 610, the processing device 140A (e.g., the obtaining module 501) may obtain an initial multi-source model of the radiation source corresponding to an energy spectrum including a plurality of energy levels.

Ideally, the radiation source may emit radiation (e.g., electron beams) of a specific energy level. Accordingly, the energy spectrum of the radiation emitted by the radiation source may also be regarded as corresponding to the specific energy level. In reality, the radiation of the radiation source may include different compositions (e.g., electrons, and/or photons) with different energy levels and an overall (or an average) energy of the different compositions may be substantially equal to the specific energy.

As described in connection with FIG. 4, the radiation source may include at least a primary source and a plurality of electron applicators. One of the plurality of electron applicators may be designated as a reference electron applicator for modeling the radiation source. For example, the radiation source may include five electron applicators of 6×6 $cm^2$, 10×10 $cm^2$, 15×15 $cm^2$, 20×20 $cm^2$, and 25×25 $cm^2$. For instance, an electron applicator of 10×10 $cm^2$ may be designated as the reference electron applicator. In such cases, the radiation source may be modeled based on the reference electron applicator. The initial multi-source model may be associated with the reference electron applicator. That is, parameters of the initial multi-source model may be set with respect to an electron applicator of 10×10 $cm^2$. In some embodiments, the reference electron applicator may also be referred to as an electron applicator for brevity.

Figure 7:
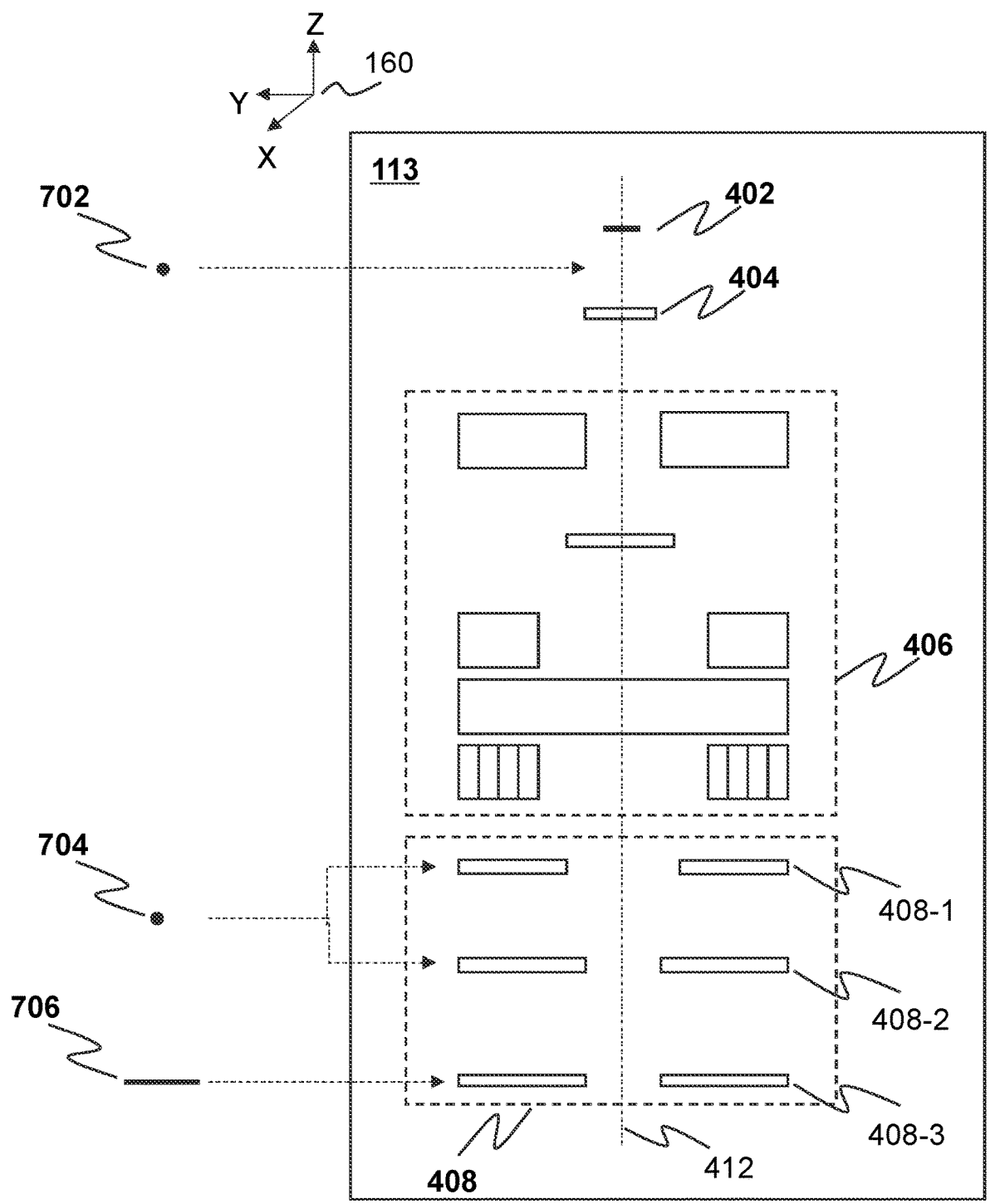
FIG. 7 illustrates a schematic diagram of exemplary virtual sources of an initial multi-source model of a radiation source according to some embodiments of the present disclosure.

In some embodiments, the initial multi-source model may include an initial phase space file that includes information of a plurality of simulated particles. The plurality of simulated particles may be used to simulate the different compositions of the radiation of the radiation source. As used herein, the radiation of the radiation source refers to electrons and/or photons exiting an electron applicator (e.g., an end opening thereof) of the radiation source. As described in connection with FIG. 4, the plurality of simulated particles may include a first portion corresponding to primary electrons generated by the primary source without being scattered within the radiation source, a second portion corresponding to primary photons generated by the primary source without interacting with other components of the radiation source within the radiation source, a third portion corresponding to secondary electrons generated by primary electrons generated by the primary source impinging on the reference electron applicator, etc. In some embodiments, the initial multi-source model may include a plurality of virtual sources corresponding to the plurality of simulated particles. For example, the initial multi-source model may include a primary virtual source and a secondary virtual source. The primary virtual source may correspond to the first portion of the simulated particles and the second portion of the simulated particles for simulating the primary source. The secondary virtual source may correspond to the third portion of the simulated particles for simulating the reference electron applicator. In some embodiments, the primary virtual source may be a point source (also referred to as a first point source) (e.g., the primary virtual source 702 as shown in FIG. 7). The primary virtual source may have an axis that coincides with the axis of the radiation source. The secondary virtual source may include a second point source (e.g., a second point source 704 as shown in FIG. 7) and a plane source (e.g., a plane source 706 as shown in FIG. 7). In some embodiments, the axis of the primary virtual source may be referred to as the axis of the radiation source for brevity. More descriptions regarding the plurality of virtual sources may be found elsewhere in the present disclosure (e.g., FIG. 7 and the description thereof).

In some embodiments, the initial phase space may include initial parameters of the plurality of virtual sources of the initial multi-source model. The initial parameters of the plurality of virtual sources may be determined based on structural parameters of the radiation source. For example, initial parameters of the primary virtual source may be determined based on one or more components of the radiation source (e.g., a target and/or a scattering foil of the radiation source). As another example, initial parameters of the second point source and/or the plane source of the secondary virtual source may be determined based on structural parameters of the reference electron applicator. More descriptions regarding the initial parameters of the plurality of virtual sources may be found elsewhere in the present disclosure (e.g., FIG. 7 and the description thereof).

In some embodiments, the processing device 140A may determine the initial phase space file of the initial multi-source model based on a direct sampling. For example, the initial phase space profile may include positions of the first portion of the simulated particles and directions of the first portion of the simulated particles. As used herein, a position of one of the first portion of the simulated particles refers to a position of the simulated particle on a first plane perpendicular to the axis of the primary virtual source (e.g., a plane parallel to the X-Y plane of the coordinate system 160 in which the primary virtual source 702 is located). The first plane may be centered where the axis of the primary virtual source intersects the first plane. A direction of one of the first portion of the simulated particles refers to an exit angle of the simulated particle from the primary virtual source with respect to the axis of the primary virtual source. An area of the first plane may relate to a size of the primary virtual source. As the first portion of the simulated particles may correspond to the first portion of the primary electrons generated by the primary source without being scattered in the radiation source and most of the first portion of the primary electrons may exit from the primary source (substantially) along the axis of the radiation source, a particle flux distribution, as a function of a distance from a center (e.g., the intersection point where the axis of the primary virtual source intersects the first plane) of the first plane or a distance from a center of a plane parallel to the first plane, of the first portion of the simulated particles may be assumed to conform to a first distribution function (e.g., a first Gaussian function). That is, the probability of any one of the first portion of the simulated particles exiting from the primary virtual source from a position close to the center of the first plane may be greater than the probability of the simulated particle exiting from the primary virtual source from a position further away from the center of the first plane; the probability of any one of the first portion of the simulated particles exiting from the primary virtual source in a direction at a first angle with the axis of the primary virtual source may be greater than the probability of the simulated particle exiting the primary virtual source in a direction at a second angle with the axis of the primary virtual source if the first angle is smaller than the second angle; the probability of any one of the first portion of the simulated particles traversing a plane parallel to the first plane at a position close to a center of the plane parallel to the first plane may be greater than the probability of the simulated particle traversing the plane parallel to the first plane at a position further away from the center of the plane parallel to the first plane.

In such cases, the processing device 140A may determine the positions of the first portion of the simulated particles or the directions of the first portion of the simulated particles by a first direct sampling based on the first distribution function. For instance, for the first portion of the simulated particles, the number (or count) of simulated particles that exit from the primary virtual source from a location of the first plane depends on the distance between the location and the center of the first plane; the smaller the distance between a location and the center of the first plane, the higher the number (or count) of simulated particles exiting the primary virtual source from the location. As another example, for the first portion of the simulated particles, the number (or count) of simulated particles that exit from the primary virtual source in a direction at an angle with the axis of the primary virtual source depends on the angle; the smaller the angle between the direction and the axis of the primary virtual source (i.e., the more the direction aligning with the axis of the primary virtual source), the higher the number (or count) of simulated particles exiting the primary virtual source along that direction. As a further example, for the first portion of the simulated particles, the number (or count) of simulated particles traversing the first plane from a location on the first plane depends on a particle flux at the location on the first plane. The particle flux at a location on the first plane refers to the number (or count) of simulated particles per unit area of the first plane (a center of which is the location) that traverses the first plane at the location on the first plane. The closer a location on the first plane to the center of the first plane, the higher the particle flux of simulated particles at the location. As further another example, for each of the first portion of the simulated particles, the processing device 140A may determine a position of the simulated particle on the first plane where the simulated particle may exit the primary virtual source by a first sub-sampling of the first sampling. The processing device 140A may determine a position of the simulated particle on the plane parallel to the first plane where the simulated particle may traverse the plane parallel to the first plane by a second sub-sampling of the first direct sampling. The processing device 140A may further determine a direction of the simulated particle based on the position of the simulated particle on the first plane and the position of the simulated particle on the plane parallel to the first plane.

As another example, the initial phase space profile may include positions of the third portion of the simulated particles and directions of the third portion of the simulated particles. In some embodiments, the third portion of the simulated particles may include a first sub-portion of simulated particles corresponding to the second point source (e.g., the second point source 704) and a second sub-portion of simulated particles corresponding to the plane source (e.g., the plane source 706). The positions of the third portion of the simulated particles may include positions of the first sub-portion of simulated particles and positions of the second sub-portion of simulated particles. The directions of the third portion of the simulated particles may include directions of the first sub-portion of simulated particles and directions of the second sub-portion of simulated particles. Similarly to the first portion of the simulated particles, a position of one of the first sub-portion of simulated particles refers to a position of the simulated particle on a second plane perpendicular to the axis of the secondary virtual source (e.g., a plane parallel to the X-Y plane of the coordinate system 160 in which the second point source 704 is located). The second plane may be centered where the axis of the secondary virtual source intersects the second plane. An area of the second plane may relate to a size of the second point source. A direction of one of the first sub-portion of simulated particles refers to an exit angle of the simulated particle from the second point source of the secondary virtual source with respect to the axis of the primary virtual source. A position of one of the second sub-portion of simulated particles refers to a position of the simulated particle on a third plane perpendicular to the axis of the secondary virtual source (e.g., a plane parallel to the X-Y plane of the coordinate system 160 in which the plane source 706 is located). The third plane may be centered where the axis of the secondary virtual source intersects the third plane. The third plane may have a same size and shape as an end opening of the reference electron applicator. A direction of each of the second sub-portion of simulated particles refers to an exit angle of the simulated particle from the plane source of the secondary virtual source with respect to the axis of the primary virtual source. As further another example, for each of the first sub-portion of simulated particles, the processing device 140A may determine a position of the simulated particle on the second plane where the simulated plane may exit the second point source by a first sub-sampling of the second sampling. The processing device 140A may determine a position of the simulated particle on the plane parallel to the second plane where the simulated particle may traverse the plane parallel to the second plane by a second sub-sampling of the second direct sampling. The processing device 140A may further determine a direction of the simulated particle based on the position of the simulated particle on the second plane and the position of the simulated particle on the plane parallel to the second plane.

In some embodiments, as the first sub-portion of simulated particles may be assumed to be generated by the second point source of the secondary virtual source and most of the first sub-portion of simulated particles may exit from the second point source (substantially) along the axis of the secondary virtual source, a particle flux distribution, as a function of a distance from a center (e.g., the intersection point where the axis of the primary virtual source intersects the second plane) of the second plane or a distance from a center of a plane parallel to the second plane, of the first sub-portion of simulated particles may be assumed to conform to a second distribution function (e.g., a second Gaussian function). That is, the probability of any one of the first sub-portion of simulated particles exiting from the second point source from a position close to a center (e.g., the intersection point where the axis of the primary virtual source intersects the second plane) of the second plane may be greater than the probability of the simulated particle exiting from the second point source from a position further away from the center of the first plane; the probability of any one of the first sub-portion of simulated particles exiting from the second point source in a direction at a third angle with the axis of the primary virtual source may be greater than the probability of the simulated particle exiting the second point source in a direction at a fourth angle with the axis of the primary virtual source if the third angle is smaller than the fourth angle; the probability of any one of the first sub-portion of the simulated particles traversing a plane parallel to the second plane at a position close to a center of the plane parallel to the second plane may be greater than the probability of the simulated particle traversing the plane parallel to the second plane at a position further away from the center of the plane parallel to the second plane. In such cases, the processing device 140A may determine the positions of the first sub-portion of simulated particles or the directions of the first sub-portion of simulated particles by a second direct sampling based on the second distribution function. For instance, for the first sub-portion of simulated particles, the number (or count) of simulated particles that exit from the second point source from a location of the second plane depends on the distance between the location and the center of the second plane; the smaller the distance between a location and the center of the first plane, the higher the number (or count) of simulated particles exiting the second point source from the location. As another example, for the first sub-portion of simulated particles, the number (or count) of simulated particles that exit from the second point source in a direction at an angle with the axis of the primary virtual source depends on the angle; the smaller the angle between the direction and the axis of the primary virtual source (i.e., the more the direction aligning with the axis of the primary virtual source), the higher the number (or count) of simulated particles exiting the primary virtual source along that direction. As a further example, for the first sub-portion of simulated particles, the number (or count) of simulated particles that exit from the second point source from a location of the second plane depends on a particle flux at the location on the second plane. The particle flux at the location on the second plane refers to the number (or count) of simulated particles per unit area of the second plane (a center of which is the location) that traverses the second plane at the location on the second plane. The closer a location on the second plane to the center of the second plane, the higher the particle flux of simulated particles at the location.

In some embodiments, as the second sub-portion of simulated particles may be assumed to be generated by the plane source of the secondary virtual source, a particle flux distribution, as a function of a distance from a center of the third plane or a distance from a center of a plane parallel to the third plane, of the second sub-portion of simulated particles may be assumed to conform to a third distribution function (e.g., a uniform function). That is, the probability of any one of the second sub-portion of simulated particles exiting from the plane source at a first position on the third plane may be equal to the probability of the simulated particle exiting from the plane source from a second position on the third plane; the probability of any one of the second sub-portion of the simulated particles exiting from the plane source in a direction at a fifth angle with the axis of the primary virtual source may be equal to the probability of the simulated particle exiting the plane source in a direction at a sixth angle with the axis of the primary virtual source; the probability of any one of the second sub-portion of the simulated particles traversing a plane parallel to the third plane at a position close to a center of the plane parallel to the third plane may be equal to the probability of the simulated particle traversing the plane parallel to the third plane at a position further away from the center of the plane parallel to the third plane. In such cases, the processing device 140A may determine the positions of the second sub-portion of simulated particles or the directions of the second sub-portion of the simulated particles by a third direct sampling based on the third distribution function. For instance, for the second sub-portion of simulated particles, the number (or count) of simulated particles that exit from the plane source from any location of the third plane may be the same. As another example, for the second sub-portion of simulated particles, the number (or count) of simulated particles that exit from the plane source in a direction at any angle with the axis of the primary virtual source may be the same. As a further example, for each of the second sub-portion of simulated particles, the processing device 140A may determine a position of the simulated particle on the third plane where the simulated plane may exit the second point source by a first sub-sampling of the third sampling. The processing device 140A may determine a position of the simulated particle on the plane parallel to the third plane where the simulated particle may traverse the plane parallel to the third plane by a second sub-sampling of the third direct sampling. The processing device 140A may further determine a direction of the simulated particle based on the position of the simulated particle on the third plane and the position of the simulated particle on the plane parallel to the third plane.

In some embodiments, before the determination of positions and directions of the plurality of simulated particles, the processing device 140A may determine the number (or count) of the plurality of simulated particles. The number of the simulated particles may be determined based on a radiation field of the radiation source. The radiation field of the radiation source may relate to an end opening of the reference electron applicator. For example, the number of the simulated particles may be determined according to equation (1):

$$N=\gamma * R/\mu^{\wedge 2}/S^{\wedge 2}, \qquad (1)$$

where N denotes the number of the simulated particles, γ denotes a constant (e.g., $10^{\wedge -3}$), R denotes an area of the radiation field of the radiation source, p denotes an uncertainty value, and S denotes a mesh size (e.g., 4 mm, 8 mm, 16 mm, etc.). R, p, and/or S may be a default setting determined by a user of the medical system. For the reference electron applicator of 10×10 cm$^2$, the area of the radiation field of the radiation source may be 10×10 cm$^2$.

In 620, the processing device 140A (e.g., the obtaining module 501, the estimation module 502, and the determination module 503) may determine a weight for each of the plurality of energy levels based on a plurality of estimated component PDD curves in a phantom corresponding to the plurality of energy levels and a measured PDD curve in the phantom corresponding to a radiation of the energy spectrum traversing the phantom.

In some embodiments, the processing device 140A may estimate, based on the initial phase space file, the plurality of component percentage depth-dose (PDD) curves in a phantom (e.g., a water phantom). Each of the plurality of component PDD curves may correspond to one of the plurality of energy levels. The processing device 140A may obtain the measured PDD curve in the phantom corresponding to the radiation of the energy spectrum traversing the phantom. For each of the plurality of energy levels, the processing device 140A may determine, based on the plurality of component PDD curves and the measured PDD curve, a weight for the each energy level. The weight for the each energy level may indicate a percentage of simulated particles of the each energy level, among the plurality of simulated particles, present in the radiation. As used herein, as the plurality of simulated particles are used to simulate the different compositions of the radiation, the plurality of simulated particles are referred to as being present in the radiation for brevity. In some embodiments, each component PDD curve and the measured PDD curve may correspond to the same electron applicator (e.g., the reference electron applicator of 10×10 cm$^2$) and the same source-skin distance (SSD) (e.g., 100 cm). As used herein, SSD refers to a distance between the primary source and a surface of the phantom (e.g., an upper surface of a water phantom) where the radiation first impinges on the phantom. More descriptions regarding the determination of the weight for the each energy level may be found elsewhere in the present disclosure (e.g., FIG. 8 and the description thereof).

Figure 9:
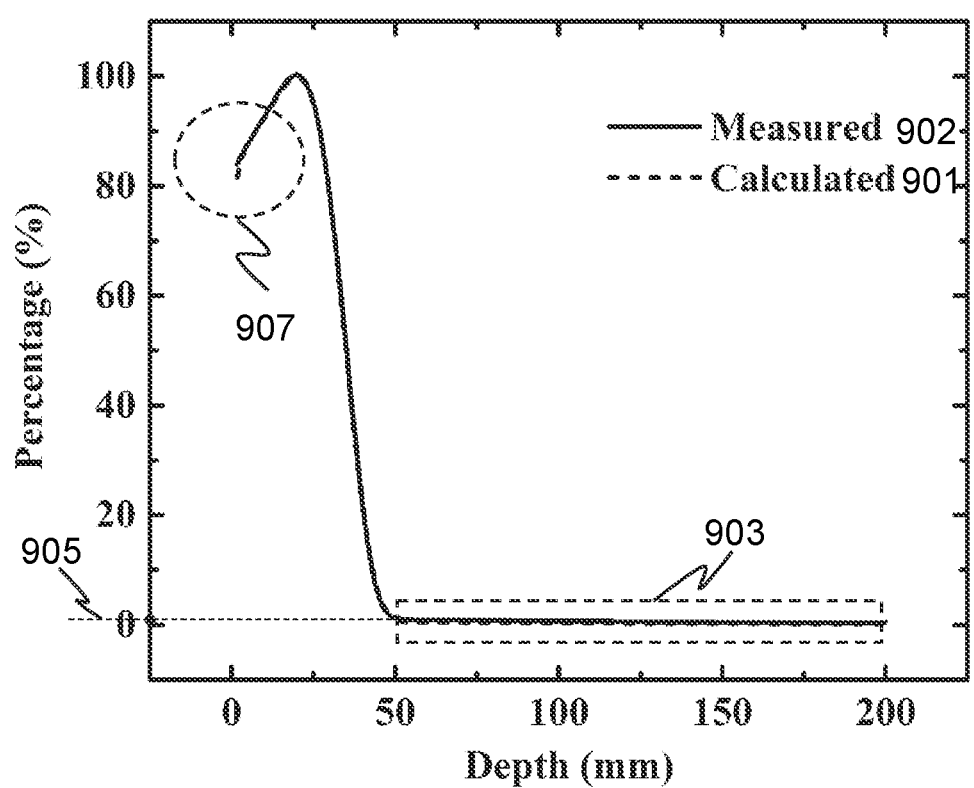
FIG. 9 is a schematic diagram 900 illustrating an exemplary measured PDD curve and a corresponding combined PDD curve according to some embodiments of the present disclosure.

In some embodiments, the processing device 140A may estimate an average energy level of photons (e.g., the third portion of primary photons) based on the energy spectrum. For example, the processing device 140A may designate the specific energy corresponding to the energy spectrum as the estimated average energy level of the photons. The processing device 140A may determine a measured average energy level of the photons based on the measured PDD curve. For example, as shown in FIG. 9, a portion (in a dashed box 903) of a measured PDD curve 901 may indicate photon contamination. The processing device 140A may designate an energy corresponding to the photon contamination (e.g., an energy denoted by a point 905 in FIG. 9) as the measured average energy level. The processing device 140A may determine, based on the estimated average energy level and the measured average energy level, a weight for the photons. The weight for the photons may be equal to a ratio between the measured average energy level and the estimated average energy level. In some embodiments, the processing device 140A may further determine the energy spectrum based on the weights for the plurality of energy levels and the weight for the photons. The energy spectrum may indicate a distribution of the plurality of energy levels in the radiation. The greater a weight for an energy level is, the higher a ratio or percentage of the energy level in the energy spectrum may be. The energy spectrum of radiation of the radiation source at a specific energy setting determined with reference to the reference electron applicator may be applied in determining a target multi-source model for the radiation source at the specific energy setting with respect to different electron applicators. According to some embodiments of the present disclosure, it is unnecessary to analyze the energy spectrum for the radiation source at the specific energy setting with respect to different electron applicators.

In 630, the processing device 140A (e.g., the obtaining module 501, the estimation module 502, and the determination module 503) may determine parameters of the primary virtual source of the initial multi-source model based on a simulated (off-axis ratio) OAR curve and a measured OAR curve corresponding to the radiation of the energy spectrum traversing the phantom.

In some embodiments, the processing device 140A may obtain the measured OAR curve corresponding to the radiation of the energy spectrum traversing the phantom. The processing device 140A may estimate (or simulate) the simulated OAR curve based on the initial parameters of the primary virtual source and the initial phase space file. The processing device 140A may determine parameters of the primary virtual source by adjusting, based on the simulated OAR curve and the measured OAR curve, the initial parameters of the primary virtual source. In some embodiments, the simulated OAR curve and the measured OAR curve may correspond to a same electron applicator (e.g., the reference electron applicator of 10×10 cm$^2$) and the same SSD (e.g., 100 cm). More descriptions regarding the determination of the parameters of the primary virtual source may be found elsewhere in the present disclosure (e.g., FIG. 10 and the descriptions thereof).

In 640, the processing device 140A (e.g., the obtaining module 501, the estimation module 502, and the determination module 503) may determine a correction coefficient for an electron applicator operably coupled to the primary source. The electron applicator may be one of the plurality of electron applicators other than the reference electron applicator.

In some embodiments, the processing device 140A may obtain an output coefficient corresponding to the electron applicator based on the reference electron applicator. The output coefficient corresponding to the electron applicator may indicate a ratio between a maximum dose corresponding to the electron applicator and a maximum dose corresponding to the reference electron applicator. The output coefficient corresponding to the electron applicator may be greater than 1 or less than 1. An output coefficient of the reference electron applicator may be equal to 1. The processing device 140A may determine a simulated output coefficient corresponding to the electron applicator based on structural parameters of the electron applicator and the energy spectrum.

The processing device 140A may further determine the correction coefficient for the electron applicator based on the output coefficient corresponding to the electron applicator and the simulated output coefficient corresponding to the electron applicator. More descriptions regarding the determination of the correction coefficient for the electron applicator may be found elsewhere in the present disclosure (e.g., FIG. 11 and the descriptions thereof).

In 650, the processing device 140A (e.g., the determination module 503) may determine a target multi-source model of the radiation source corresponding to the energy spectrum based at least in part on the initial multi-source model, the weights, the parameters of the primary virtual source, and the correction coefficient.

In some embodiments, the target multi-source model may include a target phase space file. The processing device 140A may determine the target space file by updating, based at least in part on the weights, the parameters of the primary virtual source, and the correction coefficient, the initial phase space file of the initial multi-source model. For example, the target phase space file may further include the energy spectrum determined based on the weights. As another example, the initial parameters of the primary virtual source in the initial phase space file may be updated by incorporating the parameters of the primary virtual source. As a further example, the target phase space file may further include a plurality of correction coefficients corresponding to the plurality of electron applicators. During the application of the target multi-source model, a specific correction coefficient may be selected from the plurality of correction coefficients according to a specific electron applicator.

In the traditional modeling process, a plurality of virtual sources may need to be considered and parameters of each virtual source may need to be adjusted, which is complex; a plurality of energy spectrums may need to be determined with respect to the plurality of electron applicators, respectively, which is time-consuming; and the initial phase space file may include a large amount of scattered nuclear data indicating positions and directions of the plurality of simulated particles which needs to be pre-calculated and stored, which takes storage spaces and computation resources. According to some embodiments of the present disclosure, the target multi-source model of the radiation source corresponding to the specific energy may include virtual sources less than that of traditional multi-source models. In the process of constructing the target multi-source model, the processing device 140A may determine initial parameters of the virtual sources based on structural parameters of the radiation source; determine the initial phase space file based on the direct sampling; adjust only initial parameters of the primary virtual source; and determine only one energy spectrum corresponding to a specific energy setting of the radiation source based on the reference electron applicator of the plurality of electron applicators, which make the modeling process more efficiently and accurately.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be omitted and/or one or more additional operations may be added. For example, the process 600 may further include an operation for storing information and/data (e.g., the target multi-source model) generated during the modeling process. Additionally or alternatively, the process 600 may further include an operation for determining the weight for the photons. In some embodiments, the initial multi-source model may include additional virtual sources. For example, the initial multi-source model may include a third virtual source corresponding to secondary electrons generated by the second portion of the primary electrons impinging on the collimation component 406 for simulating the collimation component 406. The third virtual source may be a line source. The plurality of simulated particles may include a fourth portion corresponding to the secondary electrons generated by the second portion of the primary electrons impinging on the collimation component 406. In some embodiments, positions and directions of the fourth portion of the simulated particles may be determined based on the direct sampling (e.g., based on a certain uniform distribution).

FIG. 7 illustrates a schematic diagram of exemplary virtual sources of an initial multi-source model of a radiation source according to some embodiments of the present disclosure. As shown in FIG. 7, the initial multi-source model of the radiation source of the treatment head 113 may include a primary virtual source and a secondary virtual source. The primary virtual source may be a point source (also referred to as a primary virtual source 702). The primary virtual source 702 may include an axis that coincides with the axis 412 of the radiation source. The secondary virtual source may correspond to a reference electron applicator (e.g., the electron applicator 408) of the radiation source. The secondary virtual source may include a second point source 704 and a plane source 706. In some embodiments, the primary virtual source 702 or the second point source 704 may include any shape. For example, the primary virtual source 702 or the second point source 704 may be a circular point source, a square point source, etc. The following descriptions are provided with reference to the primary virtual source 702 and the second point source 704 being circle point sources. It is understood that this is for illustration purposes and not intended to be limiting.

The primary virtual source 702 may include initial parameters including, e.g., a size of the primary virtual source 702, a vertical position of the primary virtual source 702 along the axis of the primary virtual source 702 (also referred to as a height position of the primary virtual source 702), a particle flux distribution of the primary virtual source 702, or the like, or any combination thereof. Merely by way of example, the size of a circular primary virtual source 702 refers to a diameter (e.g., 2 mm, 1.5 mm, etc.) of the primary virtual source 702. A particle flux of the primary virtual source 702 refers to the number (or count) of simulated particles per unit area of a fourth plane perpendicular to the axis of the primary virtual source 702. The fourth plane perpendicular to the axis of the primary virtual source 702 may also be referred to as a horizontal plane for brevity. The horizontal plane may be centered where the axis of the primary virtual source 702 intersects the horizontal plane. Accordingly, the particle flux distribution of the primary virtual source 702 refers to a distribution, as a function of a distance from the center of the horizontal plane, of a plurality of particle fluxes of the primary virtual source 702 on the horizontal plane. Similar to the particle flux distribution of the first portion of the simulated particles on the first plane as described in operation 610, the particle flux distribution of the primary virtual source 702 may be assumed to conform to a fourth distribution function (e.g., a third Gaussian function). That is, the probability of a simulated particle traversing the horizontal plane at a position close to the center (e.g., the intersection point where the axis of the primary virtual source 702 intersects the horizontal plane) of the horizontal plane may be greater than the probability of the simulated particle traversing the horizontal plane at a position further away from the center of the horizontal plane. In some embodiments, the initial parameters of the primary virtual source 702 may be determined based on structural parameters of the generator 402 and the scattering foil 404. Merely by way of example, the height position of the primary virtual source 702 may be set between the height position of the generator 402 and the height position of the scattering foil 404. As another example, the height position of the primary virtual source 702 may be set to coincide with the height position of the generator 402.

The second point source 704 may correspond to the upper part 408-1 and the middle part 408-2 of the electron applicator 408. The second point source 704 may include initial parameters including a size of the second point source 704, a vertical position of the second point source 704 along the axis of the secondary virtual source (also referred to as a height position of the second point source 704), a particle flux distribution of the second point source 704, or the like, or any combination thereof. Merely by way of example, the size of circular second point source 704 refers to a diameter (e.g., 2 mm, 1.5 mm, etc.) of the second point source 704. A particle flux of second point source 704 refers to the number (or count) of simulated particles per unit area of a fifth plane perpendicular to the axis of the secondary virtual source. The fifth plane perpendicular to the axis of the secondary virtual source may also be referred to as a second horizontal plane for brevity. The second horizontal plane may be centered where the axis of the primary virtual source intersects the second horizontal plane. Accordingly, the particle flux distribution of the second point source 704 refers to a distribution, as a function of a distance from the center of the second horizontal plane, of a plurality of particle fluxes of the second point source 704 on the second horizontal plane. Similar to the particle flux distribution of the first sub-portion of simulated particles on the second plane as described in operation 610, the particle flux distribution of the second point source 704 may be assumed to conform to a fifth distribution function (e.g., a fourth Gaussian function). That is, the probability of a simulated particle traversing the second horizontal plane at a position close to a center (e.g., the intersection point where the axis of the primary virtual source intersects the second horizontal plane) of the second horizontal plane may be greater than the probability of the simulated particle traversing the second horizontal plane at a position further away from the center of the second horizontal plane. In some embodiments, the initial parameters of the second point source 704 may be determined based on structural parameters of the electron applicator 408. Merely by way of example, the height position of the second point source 704 may be designated to coincide with a height position (e.g., a center position) between the upper part 408-1 and the middle part 408-2.

The plane source 706 may correspond to the lower part 408-3 of the electron applicator 408. The plane source 706 may include initial parameters including a size of the plane source 706, a vertical position of the plane source 706 along the axis of the primary virtual source (also referred to as a height position of the plane source 706), a particle flux distribution of the plane source 706, or the like, or any combination thereof. Merely by way of example, the size of the plane source 706 refers to both an area and the shape of the plane source 706. A particle flux of the plane source 706 refers to the number (or count) of simulated particles per unit area of a sixth plane perpendicular to the axis of the primary virtual source. The sixth plane perpendicular to the axis of the primary virtual source may also be referred to as a third horizontal plane for brevity. Accordingly, the particle flux distribution of the plane source 706 refers to a distribution, as a function of a distance from the center of the third horizontal plane, of a plurality of particle fluxes of the plane source 706 on the third horizontal plane. Similar to the particle flux distribution of the second sub-portion of simulated particles as described in operation 610, the particle flux distribution of the plane source 706 may be assumed to conform to a sixth distribution function (e.g., a second uniform function). That is, the probability of a simulated particle traversing the third horizontal plane at a first position on the third horizontal plane may be equal to the probability of the simulated particle traversing the third horizontal plane at a second position on the third horizontal plane. In some embodiments, the initial parameters of the plane source 706 may be determined based on the structural parameters of the electron applicator 408. Merely by way of example, the size of the plane source 706 may be the same as that of the end opening of the electron applicator 408. As another example, the height position of the plane source 706 may be designated to coincide with the height position of the lower part 408-3.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the radiation source of the treatment head 113 may further include a block (e.g., the block 410 as shown in FIG. 4). The processing device 140 may determine the initial parameters of the plane source 706 based further on structural parameters of the block. For example, the size of the plane source 706 may be the same as that of the opening of the block.

FIG. 8 is a flowchart illustrating an exemplary process for determining a weight from each of a plurality of energy levels of an energy spectrum of a radiation source according to some embodiments of the present disclosure. In some embodiments, process 800 may be implemented as a set of instructions (e.g., an application) stored in the storage device 150, storage 220, or storage 390. The processing device 140A, the processor 210, and/or the CPU 340 may execute the set of instructions, and when executing the instructions, the processing device 140A, the processor 210, and/or the CPU 340 may be configured to perform the process 800. The operations of the illustrated process presented below are intended to be illustrative. In some embodiments, the process 800 may be accomplished with one or more additional operations not described, and/or without one or more of the operations discussed. Additionally, the order of the operations of the process 800 illustrated in FIG. 8 and described below is not intended to be limiting. In some embodiments, the energy spectrum described elsewhere in the present disclosure (e.g., operation 620 illustrated in FIG. 6) may be obtained according to the process 800.

In 810, the processing device 140A (e.g., the estimation module 502) may estimate, based on an initial phase space file of an initial multi-source model, a plurality of component PDD curves in a phantom corresponding to a plurality of energy levels of an energy spectrum. The energy spectrum may correspond to an energy setting of a radiation source providing an average energy such as 6 MeV, 12 MeV, 18 MeV, etc. Each component PDD curve may correspond to one energy level. For example, when the average energy of the energy spectrum is 12 MeV, the plurality energy levels may include an energy of 1 MeV, 2 MeV, . . . , 12 MeV, 13 MeV, . . . , respectively. An average energy of the plurality energy levels may be 12 MeV.

The initial phase space file may correspond to a certain SSD (e.g., 100 cm). That is, the initial phase space file is determined when a distance from the simulated radiation source to the surface of the phantom (e.g., a water tank) is equal to the certain SSD. The initial phase space file may include information of a plurality of simulated particles (e.g., electrons and photons), including the energy, the position, and the velocity vector of each simulated particle. The plurality of simulated particles may be used to determine the plurality of component PDD curves. For example, the processing device 140A may calculate the plurality of component PDD curves by inputting the initial phase space file (or the information of the plurality of simulated particles) into a software such as a DOSXYZnrc software, an MCSIM software, etc. The software may output the plurality of component PDD curves.

In 820, the processing device 140A (e.g., the obtaining module 501) may obtain a measured PDD curve in the phantom corresponding to radiation of the energy spectrum traversing the phantom. The measured PDD curve may be related to the axis of the radiation source.

The measured PDD curve may be measured physically when the phantom (e.g., a water tank) is subjected to the radiation of the energy spectrum from the radiation source. Specifically, the PDD is the ratio of a radiation dose (or referred to as dose for brevity) at any depth of the phantom to dose at a fixed reference depth using a constant SSD (e.g., 100 cm). In some embodiments, the fixed reference depth may be a depth corresponding to the maximum dose. Multiple doses each of which corresponds to a point along the axis of the radiation source at a certain depth (e.g., a depth in 0 cm to 25 cm) in the phantom may be measured when the SSD is fixed. In some embodiments, the radiation source may include an electron applicator. A radiation field of the radiation source may be determined by the electron applicator. The electron applicator can be of any size (e.g., 6×6 cm², 10×10 cm², 15×15 cm², 20×20 cm², 25×25 cm², etc.). For instance, the electron applicator is of 10×10 cm². The processing device 140A may determine multiple measured PDDs based on the measured multiple doses at the multiple points along the axis at different depths and the dose of a reference point (e.g. the maximum dose point). In some embodiments, doses may be estimated (e.g., by linear interpolation) from the measured doses for the PDD. The processing device 140A may determine the measured PDD curve based on the measured PDDs with or without the estimated PDD.

In some embodiments, the dose of the point in the phantom may be measured by a dosimeter. For instance, the dosimeter may be positioned in the radiation field of the radiation source to perform the measurement. In some embodiments, the dosimeter may include a film dosimeter, an ion chamber dosimeter, a diode dosimeter, or the like, or any combination thereof.

In 830, the processing device 140A (e.g., the determination module 503) may determine, based on the plurality of component PDD curves, a combined PDD curve by adjusting at least one of a group of initial weights until a first difference between the combined PDD curve and the measured PDD curve is below a first threshold. Each initial weight may correspond to one energy level.

In some embodiments, the processing device 140A may determine a difference between the maximum absolute dose corresponding to the combined PDD curve and the maximum absolute dose corresponding to the measured PDD curve as the first difference. In some embodiments, the processing device 140A may determine the maximum deviation of each simulate PDD and the corresponding measured PDD as the first difference. Then the processing device 140A may determine whether the difference is below the first threshold (e.g., 5%, 4%, 3%, 2%, 1%, etc.). In some embodiments, the first threshold may be set according to a default setting of the medical system 100 or by a user or operator via the terminal device 130.

In some embodiments, the processing device 140A may further estimate an average energy level of photons included in the radiation of the radiation source based on the energy spectrum. The processing device 140A may determine the combined PDD curve based on the plurality of component PDD curves and the average energy level of the photons. The group of initial weights may include a plurality of weights for the plurality of component PDD curves and a weight for the photons. In some embodiments, the processing device 140A may determine a measured average energy level of the photons based on the measured PDD curve. The processing device 140A may determine, based on the estimated average energy level and the measured average energy level, a weight for the photons.

In 840, the processing device 140A (e.g., the determination module 503) may determine, based on the adjusted group of weights, the weight for each of the plurality of energy levels. The processing device 140A may designate the weight for each of the plurality of PDD curves as the weight for the corresponding energy level. The processing device 140A may store the plurality of energy levels with corresponding weights (and/or the weight for the photons) in association with the energy spectrum of the radiation source in a storage device (e.g., the storage device 150). In some embodiments, the processing device 140A may retrieval the weights of the plurality of energy levels and/or the photons to determine a target multi-source model.

It should be noted that the above description regarding the process 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be omitted and/or one or more additional operations may be added. For example, the process 800 may further include an operation to generate, based on an initial multi-source model, an initial phase space file. Additionally or alternatively, the process 800 may further include transmitting the first difference to a terminal device (e.g., the terminal device 130) of a user. The user may adjust the weight for each component PDD curve via the terminal device.

FIG. 9 is a schematic diagram 900 illustrating an exemplary measured PDD curve and a corresponding combined PDD curve according to some embodiments of the present disclosure. As shown in FIG. 9, the curve 901 represents the measured PDD curve corresponding to an energy spectrum of a radiation source, and the curve 902 represents the combined PDD curve of a plurality of component PDD curves and an average energy level of photons corresponding to the energy spectrum. According to FIG. 9, the portion in the dashed box 903 may associate with the average energy level of photons in radiation of the radiation source, indicating a photon contamination. The portions in the dashed box 907 that do not align with each other indicate a first difference between the measured PDD curve and the combined PDD curve. When the first difference is below a first threshold (e.g., 5%, 4%, 3%, 2%, 1%), the processing device 140A may determine that the weights corresponding to the component PDD curves reflected in the combined PDD curve are acceptable. The weights corresponding to the component PDD curves so determined may be assigned to corresponding energy levels such that the energy spectrum is determined.

Figure 10:
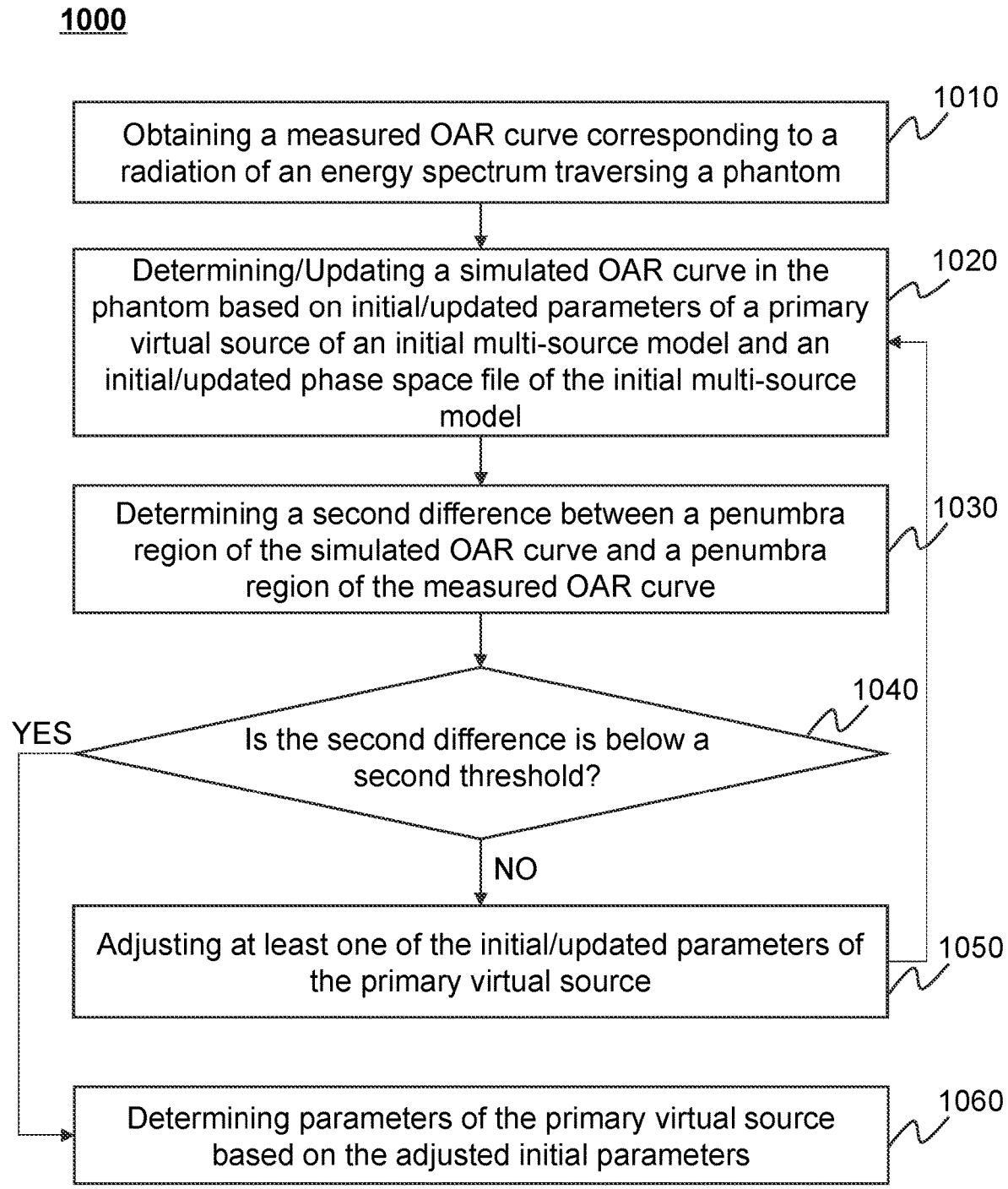
FIG. 10 is a flowchart illustrating an exemplary process for determining parameters of a primary virtual source of a target multi-source module according to some embodiments of the present disclosure.

FIG. 10 is a flowchart illustrating an exemplary process for determining parameters of a primary virtual source of a target multi-source module according to some embodiments of the present disclosure. In some embodiments, process 1000 may be implemented as a set of instructions (e.g., an application) stored in the storage device 150, storage 220, or storage 390. The processing device 140A, the processor 210, and/or the CPU 340 may execute the set of instructions, and when executing the instructions, the processing device 140A, the processor 210, and/or the CPU 340 may be configured to perform the process 1000. The operations of the illustrated process presented below are intended to be illustrative. In some embodiments, the process 1000 may be accomplished with one or more additional operations not described, and/or without one or more of the operations discussed. Additionally, the order of the operations of the process 1000 illustrated in FIG. 10 and described below is not intended to be limiting. In some embodiments, the parameters of the primary virtual source described elsewhere in the present disclosure (e.g., operation 630 illustrated in FIG. 6) may be obtained according to the process 1000.

In 1010, the processing device 140A (e.g., the obtaining module 501) may obtain a measured OAR curve corresponding to radiation of an energy spectrum traversing a phantom. The energy spectrum may correspond to an average energy (e.g., 12 MeV) of a radiation source that generates the radiation under an energy setting.

The OAR is the ratio of an off-axis dose to an axis dose (i.e., a dose of a point on the axis of the radiation source, e.g., the axis 412 of the treatment head 113) at the same depth in the phantom (e.g., a water tank) within a radiation field. The radiation field may be generated by radiation from the radiation source under an energy setting. For the radiation from a radiation source under a same energy setting, the radiation field may depend on the existence and the configuration (e.g., structural parameters) of an electron applicator of the radiation source and/or a block (e.g., a lead block) operably coupled to the electron applicator. In some embodiments, similar to the obtaining of the measured PDD curve described in operation 820 in FIG. 8, a plurality of OAR values (or referred to as OARs for brevity) at a plurality of off-axis locations at a same depth (e.g., a depth where the maximum dose occurs) may be determined based on a plurality of doses at the plurality of off-axis locations and a dose of the axis point at the same depth. As used herein, different off-axis locations at a same phantom depth (or referred to as depth for brevity) are locations that are on a same plane perpendicular to the axis along the depth of the phantom (coinciding with the axis of the radiation source) and spaced from the axis along the depth of the phantom by different distances. The processing device 140A may determine the measured OAR curve based on the plurality of OARs. In some embodiments, OAR values may be estimated (e.g., by linearly interpolation) from the measured OARs. The processing device 140A may determine the measured OAR curve based on measured OARs with or without the estimated OARs.

In 1020, the processing device 140A (e.g., the estimation module 502) may determine (or update) a simulated OAR curve in the phantom based on initial (or updated) parameters of a primary virtual source of an initial multi-source model and an initial phase space file of the initial multi-source model.

The radiation source may include a primary source and an electron applicator. The primary virtual source of the initial multi-source model may be configured to simulate the primary source. The initial phase space file may include information of a plurality of simulated particles for simulating the radiation of the primary source. In some embodiments, the initial (or updated) parameters of the primary virtual source may include a size, a position, a particle flux distribution, etc., of the primary virtual source. The size of the primary virtual source may refer to a diameter (e.g., in a range from 0 to 2 mm) of the primary virtual source. The position of the primary virtual source may refer to a position (e.g., a location along the Z-direction in the FIG. 1) of a plane that is perpendicular to the axis of the radiation source. The particle flux distribution of the primary virtual source may conform to a Gaussian distribution. In some embodiments, the initial parameters of the primary virtual source may be determined based on, e.g., a structural size and/or structural position of the primary source of the radiation source.

In some embodiments, the initial multi-source model may further include a secondary virtual source configured to simulate the electron applicator operably coupled to the primary source. The electron applicator can be of any size (e.g., 6×6 cm$^2$, 10×10 cm$^2$, 15×15 cm$^2$, 20×20 cm$^2$, 25×25 cm$^2$, etc.). For example, the electron applicator is of 10×10 cm$^2$. The simulated OAR curve may not be associated with the size of the electron applicator.

In some embodiments, similar to the determining of the simulated component PDD curves described in operation 810 in FIG. 8, the simulated OAR curve may be determined by inputting the initial phase space file (or information of a plurality of simulated particles in the initial space file) into a software such as a DOSXYZnrc software, an MCSIM software, etc. The software may output the simulated OAR curve.

In 1030, the processing device 140A (e.g., the estimation module 502) may determine a second difference between a penumbra region of the simulated OAR curve and a penumbra region of the measured OAR curve.

As used herein, a penumbra region of an OAR curve refers to a width range in which the OARs are within a threshold range (e.g., 80% to 20%, 90% to 10%, etc.). The processing device 140A may determine a degree of similarity between the penumbra region of the simulated OAR curve and the penumbra region of the measured OAR curve. The processing device 140A may determine the second difference based on the degree of similarity. In some embodiments, the processing device 140A may determine the maximum deviation of each simulated OAR and the corresponding measured OAR as the second difference.

In 1040, the processing device 140A (e.g., the estimation module 502) may determine whether the second difference is below a second threshold. In response to determining that the second difference is not below the second threshold, the processing device 140A may proceed to perform operation 1050. In response to determining that the second difference is below the second threshold, the processing device 140A may proceed to perform operation 1060.

In some embodiments, the second threshold may be set according to a default setting of the medical system 100 or by a user or operator via the terminal device 130.

In 1050, the processing device 140A (e.g., the estimation module 502) may adjust at least one of the initial parameters of the primary virtual source.

In some embodiments, the processing device 140A may receive a user input associated with the initial parameter(s) of the primary virtual source via the terminal device 130. The processing device 140A may adjust the initial parameter(s) of the primary virtual source based on the user input. In some embodiments, the processing device 140A may adjust the initial parameter(s) of the primary virtual source automatically. Then, the processing device 140A may repeat operation 1020 to determine an updated simulated OAR based on the updated parameters of the primary virtual source, until the second difference is below the second threshold.

In 1060, the processing device 140A (e.g., the determination module 503) may determine parameters of the primary virtual source based on the adjusted initial parameters. The processing device 140A may designate the adjusted initial parameters as the parameters of the primary virtual source.

In some embodiments, the processing device 140A may store the parameters of the primary virtual source in association with the energy spectrum of the radiation source in a storage device (e.g., the storage device 150). The processing device 140A may determine a target multi-source model based on the parameters of the primary virtual source.

It should be noted that the above description regarding the process 1000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be omitted and/or one or more additional operations may be added. For example, the process 1000 may further include an operation to obtain structural parameters of the radiation source. Additionally or alternatively, the process 1000 may further include an operation for generating the initial phase space file based on the initial multi-source model.

FIG. 11 is a flowchart illustrating an exemplary process for determining a correction coefficient corresponding to an electron applicator according to some embodiments of the present disclosure. In some embodiments, process 1100 may be implemented as a set of instructions (e.g., an application) stored in the storage device 150, storage 220, or storage 390. The processing device 140A, the processor 210, and/or the CPU 340 may execute the set of instructions, and when executing the instructions, the processing device 140A, the processor 210, and/or the CPU 340 may be configured to perform the process 1100. The operations of the illustrated process presented below are intended to be illustrative. In some embodiments, the process 1100 may be accomplished with one or more additional operations not described, and/or without one or more of the operations discussed. Additionally, the order of the operations of the process 1100 illustrated in FIG. 11 and described below is not intended to be limiting. In some embodiments, the parameters of the correction coefficient for the electron applicator described elsewhere in the present disclosure (e.g., operation 640 illustrated in FIG. 6) may be obtained according to the process 1100.

In 1110, the processing device 140A (e.g., the obtaining module 501) may obtain an output coefficient corresponding to each of a plurality of electron applicators. As used herein, a specific output coefficient corresponding to a specific electron applicator refers to a ratio of a dose at the maximum dose point measured under the specific electron applicator to a dose at the maximum dose point measured under a reference electron applicator. For example, when the reference electron applicator is of $10 \times 10$ cm$^2$, and a dose at the maximum dose point corresponding to the reference electron applicator is x, a dose at the maximum dose point corresponding to an electron applicator of $15 \times 15$ cm$^2$ is y, the output coefficient of the electron applicator of $15 \times 15$ cm$^2$ may be determined as x/y. As another example, when the reference electron applicator is of $10 \times 10$ cm$^2$, the output coefficient of an electron applicator of $10 \times 10$ cm$^2$ may be determined as 1.

In some embodiments, different electron applicators may correspond to different output coefficients. Each electron applicator may be operably coupled to a same primary source of a radiation source that generates radiation corresponding to an energy setting (e.g., 12 MeV). The energy setting of the radiation source may correspond to an energy spectrum. Then the output coefficient corresponding to the electron applicator may be determined under an SSD (e.g., 100 cm).

In 1120, the processing device 140A (e.g., the determination module 503) may determine a simulated output coefficient corresponding to each of the plurality of electron applicators based on structural parameters of the electron applicator.

The structural parameters of the electron applicator may include a size, a position, or the like, or a combination thereof. The size (e.g., $6 \times 6$ cm$^2$, $10 \times 10$ cm$^2$, $15 \times 15$ cm$^2$, etc.) of the electron applicator, evaluated by way of the size of the end opening of the electron applicator, may relate to a radiation field of the radiation source. In some embodiments, the electron applicator may be operably coupled with a block (e.g., the block 410 as shown in FIG. 4). The radiation field of the radiation source may be associated with the shape and/or size of the block. In such case, the structural parameters of the electron applicator may further include a shape and/or size of the block.

The processing device 140A may obtain a specific multi-source model from a storage device (e.g., the storage device 150). The specific multi-source model may be similar to the initial multi-source model as described in FIG. 8 or 10. For example, the specific multi-source model may include a specific primary virtual source for simulating the primary source and a specific secondary virtual source for simulating the electron applicator of the radiation source. Parameters (e.g., a size, a size, a position) of the specific primary virtual source may be determined according to process 1000 as described in FIG. 10. The processing device 140A may generate a specific phase space file corresponding to a specific electron applicator based on the specific multi-source model. In some embodiments, similar to the determining of the simulated component PDD curves described in operation 810 in FIG. 8, the simulated output coefficient corresponding to the electron applicator may be determined based on the specific phase space file (or information of a plurality of simulated particles in the specific phase space file). For instance, the simulated output coefficient corresponding to the electron applicator may be determined by inputting the specific phase space file (or information of a plurality of simulated particles in the specific phase space file) into a software such as a DOSXYZnrc software, an MCSIM software, etc. The software may output the output coefficient corresponding to the specific electron applicator.

In 1130, the processing device 140A (e.g., the determination module 503) may determine a correction coefficient for each of the plurality of electron applicators based on the output coefficient and the simulated output coefficient.

As used herein, a correction coefficient for the electron applicator may be used to correct the output coefficient corresponding to the second electron applicator. For example, when the simulated output coefficient of the specific electron applicator is m, and the output coefficient corresponding the specific electron applicator is n, the processing device 140A may determine the correction coefficient for the specific electron applicator as n. The processing device 140A may store the correction coefficient for each of the plurality of electron applicators for further purposes, for example, for correcting the output coefficient of a certain electron applicator during a treatment using the radiation source with the certain electron applicator.

It should be noted that the above description regarding the process 1100 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be omitted and/or one or more additional operations may be added. For example, the process 1100 may further include an operation for storing information and/or data (e.g., the correction coefficient for each second electron applicator) in the storage device 150.

FIG. 12 is a flowchart illustrating an exemplary process for determining a dose distribution in an object according to some embodiments of the present disclosure. In some embodiments, process 1200 may be implemented as a set of instructions (e.g., an application) stored in the storage device 150, storage 220, or storage 390. The processing device 140B, the processor 210, and/or the CPU 340 may execute the set of instructions, and when executing the instructions, the processing device 140B, the processor 210, and/or the CPU 340 may be configured to perform the process 1200. The operations of the illustrated process presented below are intended to be illustrative. In some embodiments, the process 1200 may be accomplished with one or more additional operations not described, and/or without one or more of the operations discussed. Additionally, the order of the operations of the process 1200 illustrated in FIG. 12 and described below is not intended to be limiting.

In 1210, the processing device 140B (e.g., the obtaining module 504) may obtain structural parameters of an electron applicator of a radiation source.

The radiation source may have an axis perpendicular to an exit of the radiation source. The radiation source may further include a primary source. More descriptions about the radiation source may be found elsewhere of the present disclosure (e.g., FIGS. 4 and 6 and the description thereof).

In some embodiments, the structural parameters of the electron applicator may include a size, a position, or the like, or a combination thereof. In some embodiments, the position of the electron applicator may refer to a location of the central point of the electron applicator along the direction of the exit of the radiation source. The size (e.g., 6×6 cm², 10×10 cm², 15×15 cm², etc.) of an end opening of the electron applicator may relate to a radiation field of the radiation source. In some embodiments, the electron applicator may be operably coupled with a block (e.g., the block 410 as shown in FIG. 4). The radiation field of the radiation source may be associated with the shape and/or size of the block. In such case, the structural parameters of the electron applicator may further include a shape and/or size of the block.

In 1220, the processing device 140B (e.g., the obtaining module 504) may obtain a target multi-source model of the radiation source corresponding to an energy spectrum.

The energy spectrum of the radiation source may correspond to a specific energy setting such as 6 MeV, 12 MeV, 18 MeV, etc. The radiation source may include a plurality of energy levels corresponding to a plurality of weights. The weights of the plurality of energy levels may correspond to the specific energy setting.

The target multi-source model may include at least a primary virtual source corresponding to the primary source, and a secondary virtual source corresponding to the electron applicator. The primary virtual source may be a first point source, and the secondary virtual source may include a second point source and a plane source. For example, the electron applicator includes an upper part, a middle part, and a lower part, the second point source may correspond to the upper part and the middle part of the electron applicator. The plane source may correspond to the lower part of the electron applicator. More descriptions regarding the target multi-source model of the radiation source may be found elsewhere of the present disclosure (e.g., FIGS. 6 and 7 and the descriptions thereof).

In 1230, the processing device 140B (e.g., the determination module 505) may determine, based on the target multi-source model and the structural parameters of the electron applicator, a phase space file including information of a plurality of simulated particles corresponding to radiation of the radiation source.

As used herein, the radiation of the radiation source refers to electrons and/or photons exiting an end opening of the electron applicator traversing the subject. In some embodiments, the radiation of the radiation source may include primary electrons, photons, and secondary electrons. The primary electrons and the photons may be generated by the primary source. The primary electrons may include a first portion that exit the radiation source without being scattered in the radiation source and a second portion. The secondary electrons may be generated by the second portion of the primary electrons impinging on the electron applicator. A first portion of the simulated particles may correspond to the first portion of primary electrons, a second portion of the simulated particles may correspond to the photons, and a third portion of the simulated particles may correspond to the secondary electrons.

In some embodiments, the information of the plurality simulated particles included in the phase space file may include a position, a direction, an energy, etc., of each of the plurality of simulated particles. In some embodiments, the processing device 140B may input the structural parameters of the electron applicator into the target multi-source model. The simulated particles in the phase space file may be determined based on a direct sampling (e.g., a random direct sampling). More descriptions regarding the determining the phase space file corresponding to the radiation source may be found elsewhere of the present disclosure (e.g., FIG. 13 and the descriptions thereof).

In 1240, the processing device 140B (e.g., the obtaining module 504) may obtain a transport model of the radiation of the energy spectrum traversing an object.

The transport model may be configured to simulate a particle transport of the plurality of simulated particles. In some embodiments, the transport model may include a Monte Carlo (MC) algorithm, a Voxel Monte Carlo (VMC) algorithm, a Macro Monte Carlo (MMC) algorithm, or the like, or any combination thereof.

In 1250, the processing device 140B (e.g., the determination module 505) may determine a dose distribution in the object based on the phase space file and the transport model.

In some embodiments, the processing device 140B may input the phase space file (or the information of the plurality of simulated particles) into the transport model. In some embodiments, the energy spectrum of the radiation source, the spatial distribution, angular distribution, etc. of simulated particles in the radiation field of the radiation source may be inputted into the transport model. According to the inputted information, transports of the plurality of simulated particles may be simulated based on the transport model. Then the transport model may output a plurality of doses of a plurality of locations in the object (e.g., a patient) corresponding to the electron applicator. The processing device 140B may determine a dose distribution (e.g., a 3D dose distribution) in the object based on the plurality of doses. In some embodiments, the processing device 140B may determine a corrected dose of each of the plurality of locations in the object based on a correction coefficient corresponding to the electron applicator. The determination of the correction coefficient corresponding to the electron applicator may be described in connection with FIG. 11. Then the processing device 140B may determine an updated dose distribution in the object based on the corrected doses. The processing device 140B may determine the updated dose distribution as the dose distribution of the object. In some embodiments, the dose distribution in the object may be represented using a plurality of dose distribution curves (e.g., the dose distribution curves illustrated in FIG. 14).

It should be noted that the above description regarding the process 1200 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be omitted and/or one or more additional operations may be added. For example, the process 1200 may further include an operation for obtaining a CT image of the object (e.g., the patient) to determine a shape of a region of interest (ROI). Additionally or alternatively, the process 1200 may further include transmitting the dose distribution of the object to a terminal device (e.g., the terminal device 130) of a user. The user may view the dose distribution via the terminal device for further treatment.

FIG. 13 is a flowchart illustrating an exemplary process for determining a phase space file of a target multi-source model according to some embodiments of the present disclosure. In some embodiments, process 1300 may be implemented as a set of instructions (e.g., an application) stored in the storage device 150, storage 220, or storage 390. The processing device 1406, the processor 210, and/or the CPU 340 may execute the set of instructions, and when executing the instructions, the processing device 140B, the processor 210, and/or the CPU 340 may be configured to perform the process 1300. The operations of the illustrated process presented below are intended to be illustrative. In some embodiments, the process 1300 may be accomplished with one or more additional operations not described, and/or without one or more of the operations discussed. Additionally, the order of the operations of the process 1300 illustrated in FIG. 13 and described below is not intended to be limiting. Operation 1230 in the process 1200 may be achieved by performing one or more operations of the process 1300.

As described in connection with FIG. 6, the target multi-source model of the radiation source may include a target phase space file. As the target multi-source model is determined based on a reference electron applicator, the target phase space file may be associated with the reference electron applicator. If an electron applicator operably coupled to the primary source of the radiation source is the same as the reference electron applicator, the processing device 140B may designate the target phase space file as the phase space file for determining the dose distribution in the object. Alternatively, if the electron applicator is different from the reference electron applicator, the processing device 140B may determine the phase space file, especially information of the plurality of simulated particles of the phase space file, based on the target phase space file and structural parameters of the electron applicator according to the process 1300.

In 1310, the processing device 140B (e.g., the determination module 505) may determine positions and directions of the plurality of simulated particles based on structural parameters of the electron applicator.

Similar to the initial phase space file as described in operation 610, the plurality of simulated particles in the phase space file may include a first portion corresponding to primary electrons without being scattered in the radiation source, a second portion corresponding to photons, and a third portion corresponding to secondary electrons corresponding to the electron applicator. The second portion of the simulated particles may include a first sub-portion of simulated particles corresponding to the second point source of the target multi-source model and a second sub-portion of simulated particles corresponding to the plane source of the target multi-source model.

Similar to the determination of the initial phase space file as described in operation 610, for each of the first portion of the simulated particles, the processing device 140B may determine a position and a direction of the simulated particle by a fourth direct sampling based on a seventh distribution function (e.g., a fifth Gaussian function) in a similar manner as that as described in connection with operation 610. For each of the first sub-portion of simulated particles, the processing device 140B may determine a position and a direction of the simulated particle by a fifth direct sampling based on an eighth distribution function (e.g., a sixth Gaussian function). For each of the second sub-portion of simulated particles the processing device 140B may determine a position and a direction of the simulated particle by a sixth based on a ninth distribution function (e.g., a third uniform distribution function). In some embodiments, the processing device 140B may designate positions and directions of the first portion of the simulated particles in the target phase space file as that in the phase space file, which is similar to the determination of the initial phase space file as described in operation 610.

In 1320, the processing device 140B (e.g., the determination module 505) may determine particle energies of the plurality of simulated particles based on the target multi-source model.

In some embodiments, the processing device 140B may obtain the energy spectrum from the target phase space file of the target multi-source model. The processing device 140B may determine the particle energy of one of the plurality of simulated particles by a tenth direct sampling from the energy spectrum based on the weights for the plurality of energy level. That is, the higher the weight for an energy level is, the higher the probability for the energy level being sampled may be. For instance, the processing device 140B may sample the energy spectrum based on the weights, and determine the particle energy of one of the plurality of simulated particles based on the sampling.

In 1330, the processing device 140B (e.g., the determination module 505) may determine the phase space file based on the positions, the directions, and the energies.

In some embodiments, the processing device 140B may update the target phase file based on the positions, the directions, and the particle energies. The processing device 140B may designate the updated target phase file as the phase file.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the process 1300 may include one or more additional operations. For example, an operation for updating parameters of the secondary virtual source in the target phase space file of the target multi-source model may be added before operation 1330 of the process 1300. The parameters of the secondary virtual source may be updated based on the structural parameters of the electron applicator. The processing device 140B may determine the phase space file based further on the updated parameters of the secondary virtual source. In some embodiments, one operation of the process 1300 may be achieved by performing two sub-operations. For example, the processing device 140B may determine the positions of the plurality of simulated particles and the directions of the plurality of simulated particles separately.

Figure 14:
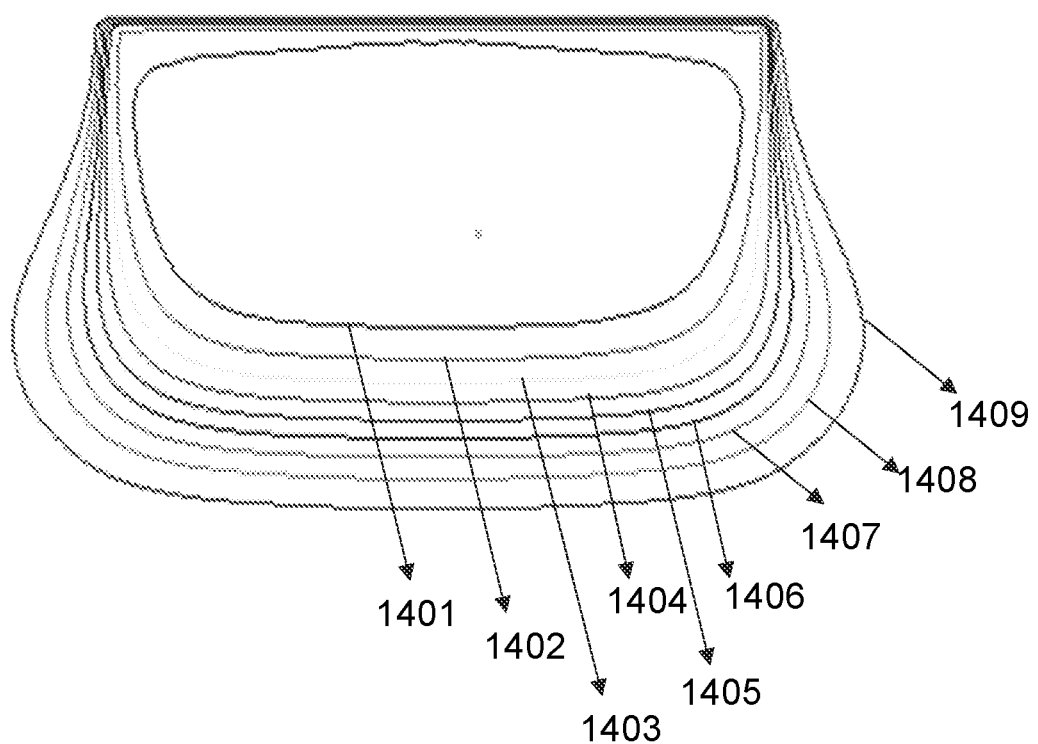
FIG. 14 is a schematic diagram illustrating an exemplary dose distribution curve in a phantom according to some embodiments of the present disclosure.

FIG. 14 is a schematic diagram illustrating an exemplary dose distribution curve in a phantom according to some embodiments of the present disclosure. As shown in FIG. 14, the curves 1401, 1402, 1403, 1404, 1405, 1406, 1407, 1408, and 1409 represent different dose distribution curves each of which corresponds to a depth in the phantom, respectively. According to FIG. 14, a line passing through the central axis of the different dose distribution curves may have a plurality of intersection points with the dose distribution curves. The processing device 140B may determine a PDD curve based on the corresponding doses of the plurality of intersection points.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A system, comprising:
   a storage device storing a set of instructions for modeling a radiation source configured to emit radiation of an energy spectrum that includes a plurality of energy levels; and
   at least one processor in communication with the storage device, wherein when executing the set of instructions, the at least one processor is configured to cause the system to perform operations including:
      obtaining an initial multi-source model of the radiation source, wherein the initial multi-source model includes an initial phase space file that includes information of a plurality of simulated particles of the plurality of energy levels;
      estimating, based on the initial phase space file, a plurality of component percentage depth-dose (PDD) curves in a phantom, wherein each of the plurality of component PDD curves corresponds to one of the plurality of energy levels;
      obtaining a measured PDD curve in the phantom corresponding to the radiation of the energy spectrum traversing the phantom;
      for each of the plurality of energy levels, determining, based on the plurality of component PDD curves and the measured PDD curve, a weight for the each energy level indicating a percentage of simulated particles of the each energy level, among the plurality of simulated particles, present in the radiation; and
      determining a target multi-source model of the radiation source corresponding to the energy spectrum based at least in part on the initial multi-source model and the weights.

2. The system of claim 1, wherein
   the initial phase space file includes a group of initial weights each of which corresponds to one of the plurality of energy levels, and
   the determining a weight for each of the plurality of energy levels includes:
      determining, based on the plurality of component PDD curves, a combined PDD curve by adjusting at least one of the group of initial weights until a first difference between the combined PDD curve and the measured PDD curve is below a first threshold; and
      determining, based on the adjusted group of weights, the weight for each of the plurality of energy levels.

3. The system of claim 1, wherein
   the radiation source includes a primary source and an electron applicator, and
   the radiation includes primary electrons and secondary electrons, the primary electrons being generated by the primary source, the primary electrons including a first portion that exit the radiation source without being scattered and a second portion, and the secondary electrons being generated by the second portion of the primary electrons impinging on the electron applicator.

4. The system of claim 3, wherein
   a first portion of the simulated particles correspond to the first portion of primary electrons;
   the radiation further includes photons, and
   a second portion of the simulated particles correspond to the photons.

5. The system of claim 4, wherein the photons are generated by the primary source.

6. The system of claim 4, wherein the initial multi-source model of the radiation source includes a primary virtual source corresponding to the first portion of the simulated particles and the second portion of the simulated particles for simulating the primary source.

7. The system of claim 6, wherein the initial phase space file includes positions of the first portion of the simulated particles and directions of the first portion of the simulated particles.

8. The system of claim 7, wherein the positions of the first portion of the simulated particles or the directions of the first portion of the simulated particles are determined by a direct sampling based on a first distribution function, a particle flux distribution of the first portion of the simulated particles on a plane perpendicular to an axis of the primary virtual source conforming to the first distribution function.

9. The system of claim 6, wherein
   a third portion of the simulated particles corresponding to the secondary electrons, and
   the initial multi-source model of the radiation source includes a secondary virtual source corresponding to the third portion of the simulated particles for simulating the electron applicator.

10. The system of claim 9, wherein the initial phase space file includes positions of the third portion of the simulated particles and directions of the third portion of the simulated particles.

11. The system of claim 9, wherein the secondary virtual source includes at least one of a second point source or a plane source,
    the third portion of simulated particles includes a first sub-portion of simulated particles corresponding to the second point source and a second sub-portion of simulated particles corresponding to the plane source,
    positions of the first sub-portion of simulated particles or directions of the first sub-portion of simulated particles being determined by a second direct sampling based on a second distribution function, wherein a particle flux distribution of the first sub-portion of simulated particles on a second plane perpendicular to the axis of the primary virtual source conforms to the second distribution function, and
    positions of the second sub-portion of simulated particles or directions of the second sub-portion of simulated particles being determined by a third direct sampling based on a third distribution function, wherein a flux distribution of the second sub-portion of simulated particles on a third plane perpendicular to the axis of the primary virtual source conforms to the third distribution.

12. The system of claim 6, wherein the at least one processor is further configured to cause the system to perform the operations including:
obtaining a measured off-axis ratio (OAR) curve corresponding to the radiation of the energy spectrum traversing the phantom;
determining a simulated OAR curve in the phantom based on parameters of the primary virtual source of the initial multi-source model and the initial phase space file;
adjusting the parameters of the primary virtual source until a second difference between a penumbra region of the simulated OAR curve and a penumbra region of the measured OAR curve is below a second threshold; and
determining the target multi-source model of the radiation source based further on the adjusted parameters of the primary virtual source.

13. The system of claim 12, wherein the parameters of the primary virtual source include at least one of a size of the primary virtual source, a vertical position of the primary virtual source along the axis of the primary virtual source, or a particle flux distribution of the primary virtual source.

14. The system of claim 3, wherein
the primary source is configured to be operably coupled to one of a plurality of second electron applicators, and
the at least one processor is further configured to cause the system to perform the operations including:
for each of the plurality of second electron applicators,
obtaining an output coefficient corresponding to the second electron applicator;
determining a simulated output coefficient corresponding to the second electron applicator based on structural parameters of the second electron applicator; and
determining a correction coefficient for the second electron applicator based on the output coefficient and the simulated output coefficient.

15. The system of claim 1, wherein the determining a weight for each of the plurality of energy levels includes:
receiving a user input relating to the weight for the energy level; and
determining the weight for the energy level based at least in part on the user input.

16. The system of claim 4, wherein the at least one processor is further configured to direct the system to perform operations including:
estimating an average energy level of the photons based on the energy spectrum;
determining a measured average energy level of the photons based on the measured PDD curve;
determining, based on the estimated average energy level and the measured energy level, a weight for the photons; and
determining the target multi-source model based further on the weight for the photons.

17. The system of claim 9, wherein the secondary virtual source includes at least one of a second point source or a plane source,
the electron applicator includes at least an upper part, a middle part, and a lower part,
the second point source corresponds to the upper part and the middle part of the electron applicator, and
the plane source corresponds to the lower part of the electron applicator.

18. The system of claim 1, wherein
the radiation source includes a collimation component, and
the initial multi-source model of the radiation source further includes a third virtual source corresponding to the collimation component.

19. A method for modeling a radiation source configured to emit radiation of an energy spectrum that includes a plurality of energy levels, the method being implemented on a computing device including at least one processor and at least one storage device, the method comprising:
obtaining an initial multi-source model of the radiation source, wherein the initial multi-source model includes an initial phase space file that includes information of a plurality of simulated particles of the plurality of energy levels;
estimating, based on the initial phase space file, a plurality of component percentage depth-dose (PDD) curves in a phantom, wherein each of the plurality of component PDD curves corresponds to one of the plurality of energy levels;
obtaining a measured PDD curve in the phantom corresponding to the radiation of the energy spectrum traversing the phantom;
for each of the plurality of energy levels, determining, based on the plurality of component PDD curves and the measured PDD curve, a weight for the each energy level indicating a percentage of simulated particles of the each energy level, among the plurality of simulated particles, present in the radiation; and
determining a target multi-source model of the radiation source corresponding to the energy spectrum based at least in part on the initial multi-source model and the weights.

20. A non-transitory computer readable medium, comprising executable instructions that, when executed by at least one processor, direct the at least one processor to perform a method for modeling a radiation source configured to emit radiation of an energy spectrum that includes a plurality of energy levels, the method comprising:
obtaining an initial multi-source model of the radiation source, wherein the initial multi-source model includes an initial phase space file that includes information of a plurality of simulated particles of the plurality of energy levels;
estimating, based on the initial phase space file, a plurality of component percentage depth-dose (PDD) curves in a phantom, wherein each of the plurality of component PDD curves corresponds to one of the plurality of energy levels;
obtaining a measured PDD curve in the phantom corresponding to the radiation of the energy spectrum traversing the phantom;
for each of the plurality of energy levels, determining, based on the plurality of component PDD curves and the measured PDD curve, a weight for the each energy level indicating a percentage of simulated particles of the each energy level, among the plurality of simulated particles, present in the radiation; and
determining a target multi-source model of the radiation source corresponding to the energy spectrum based at least in part on the initial multi-source model and the weights.

* * * * *